US010105080B1

(12) United States Patent
Kam et al.

(10) Patent No.: US 10,105,080 B1
(45) Date of Patent: Oct. 23, 2018

(54) INTERSTITIAL FLUID SAMPLING ABOVE MICRONEEDLE ARRAY

(71) Applicant: Verily Life Sciences LLC, Mountain View, CA (US)

(72) Inventors: Kimberly Kam, Mountain View, CA (US); Jerrod Joseph Schwartz, San Francisco, CA (US); Gary Tong, Berkeley, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 438 days.

(21) Appl. No.: 14/583,978

(22) Filed: Dec. 29, 2014

Related U.S. Application Data

(60) Provisional application No. 62/068,417, filed on Oct. 24, 2014.

(51) Int. Cl.
| | |
|---|---|
| *A61B 5/1455* | (2006.01) |
| *A61B 5/145* | (2006.01) |
| *A61B 10/00* | (2006.01) |
| *A61B 5/00* | (2006.01) |

(Continued)

(52) U.S. Cl.
CPC ........ *A61B 5/14514* (2013.01); *A61B 5/1455* (2013.01); *A61B 5/14539* (2013.01); *A61B 5/4839* (2013.01); *A61B 5/6833* (2013.01); *A61B 10/0045* (2013.01); *A61M 5/158* (2013.01); *A61M 5/1723* (2013.01); *A61B 2010/008* (2013.01); *A61M 2005/1726* (2013.01)

(58) Field of Classification Search
CPC ... A61B 5/0059; A61B 5/1459; A61B 5/0071; A61B 5/14532; G01N 21/6428
See application file for complete search history.

(56) References Cited

U.S. PATENT DOCUMENTS

| | | | | |
|---|---|---|---|---|
| 6,107,099 A | * | 8/2000 | Munkholm | G01N 31/22 422/400 |
| 6,379,969 B1 | * | 4/2002 | Mauze | G01N 21/6428 422/82.05 |
| 7,344,499 B1 | * | 3/2008 | Prausnitz | A61B 5/150022 600/309 |

(Continued)

FOREIGN PATENT DOCUMENTS

WO      WO 2013186628 A1  * 12/2013 ........... A61B 5/6813

*Primary Examiner* — Eric Winakur
(74) *Attorney, Agent, or Firm* — Kilpatrick Townsend & Stockton LLP

(57) ABSTRACT

Devices are provided that include a plurality of microneedles that penetrate skin and that receive interstitial fluid from the skin tissue. The microneedles are further configured to direct the received interstitial fluid to nanosensors configured to change an optical property based on interaction with an analyte in the received interstitial fluid, allowing optical detection of the analyte. Direction of the received interstitial fluid to the nanosensors can be facilitated by a pump configured to control the flow rate of the interstitial fluid through the microneedles. Such devices could be configured to detect the analyte independently or in combination with a reader device configured to be periodically mounted to the devices and to detect the analyte. Further, such devices can include delivery systems configured to transdermally deliver a drug or other substance into or through the skin in response to a detected concentration, presence, or other property of the analyte.

19 Claims, 7 Drawing Sheets

(51) Int. Cl.
    *A61M 5/158*    (2006.01)
    *A61M 5/172*    (2006.01)

(56) References Cited

U.S. PATENT DOCUMENTS

| | | | |
|---|---|---|---|
| 8,470,300 B2 * | 6/2013 | Clark | B82Y 15/00 |
| | | | 424/417 |
| 8,575,663 B2 | 11/2013 | Lieber et al. | |
| 8,898,069 B2 | 11/2014 | Hood et al. | |
| 2004/0086897 A1 * | 5/2004 | Mirkin | C12Q 1/6816 |
| | | | 435/6.12 |
| 2007/0191696 A1 * | 8/2007 | Mischler | A61B 5/157 |
| | | | 600/310 |
| 2007/0264623 A1 | 11/2007 | Wang et al. | |
| 2007/0276211 A1 * | 11/2007 | Mir | A61B 5/14532 |
| | | | 600/345 |
| 2008/0125743 A1 * | 5/2008 | Yuzhakov | A61M 37/0015 |
| | | | 604/506 |
| 2009/0247984 A1 * | 10/2009 | Lamego | A61B 5/14532 |
| | | | 604/506 |
| 2010/0312191 A1 * | 12/2010 | Allen | A61B 5/1411 |
| | | | 604/173 |
| 2011/0160069 A1 * | 6/2011 | Corrie | A61B 17/205 |
| | | | 506/7 |
| 2011/0230736 A1 | 9/2011 | Tepper et al. | |
| 2011/0294685 A1 | 12/2011 | O'Halloran | |
| 2013/0197326 A1 | 8/2013 | Dubach et al. | |
| 2014/0336487 A1 * | 11/2014 | Wang | A61B 5/685 |
| | | | 600/352 |
| 2015/0202418 A1 * | 7/2015 | Simon | A61B 10/0045 |
| | | | 604/319 |

* cited by examiner

US 10,105,080 B1

INTERSTITIAL FLUID SAMPLING ABOVE MICRONEEDLE ARRAY

CROSS-REFERENCE TO RELATED APPLICATION

This application claims priority to U.S. Provisional Patent Application No. 62/068,417, filed Oct. 24, 2014, which is incorporated herein by reference.

BACKGROUND

Unless otherwise indicated herein, the materials described in this section are not prior art to the claims in this application and are not admitted to be prior art by inclusion in this section.

Certain medical states or conditions of a human body can be detected using sensors disposed within the human body (e.g., implanted within and/or penetrating skin of the human body) and/or by extracting a fluid or tissue (e.g., by extracting a sample of blood using, e.g., a syringe, by biopsying a portion of tissue) for analysis outside of the human body. Some medical states or conditions can change slowly, occur rarely, or otherwise indicate that monitoring of the human body over an extended period of time is preferred. For example, a level of glucose in blood of an individual with diabetes could be monitored at a plurality of points in time. A sensor implanted within the human body could enable long-term monitoring of a medical state or condition of the body of a wearer while allowing the wearer to perform activities of daily living, to travel, to commute, or to engage in other activities with minimal interruption. Additionally or alternatively, a target fluid (e.g., blood) could be extracted transdermally (e.g., using a syringe, lancet, or other instrument) a plurality of times. Such monitoring could be performed preventatively, e.g., to monitor an otherwise healthy wearer's health state over time to enable early detection of an adverse medical condition, to develop data describing a 'healthy' baseline state of the wearer, or to enable other applications. Medical states or conditions of a human body monitored via detection of one or more properties of a fluid or tissue within the human body can include electrolyte concentrations (e.g., chloride, potassium, calcium, sodium), glucose or other metabolite concentrations (e.g., urea, creatinine), blood oxygenation, or other information about the body of a wearer.

SUMMARY

Some embodiments of the present disclosure provide a system including: (i) a plurality of nanosensors, wherein each nanosensor includes a nanoparticle and is configured to selectively interact with an analyte present in interstitial fluid, and wherein each nanosensor is further configured to have an optical property that changes in response to interaction with the analyte; (ii) a detector, wherein the detector is configured to optically detect the optical property of the nanosensors; (iii) a plurality of microneedles, wherein each microneedle includes (A) a first end configured to penetrate skin, (B) a second end opposite the first end, and (C) a channel that extends from a first opening proximate the first end to a second opening proximate the second end such that interstitial fluid is received into the channel via the first opening when the microneedle penetrates the skin, and wherein the nanosensors are disposed relative to the microneedles such that the microneedles direct the received interstitial fluid to the nanosensors via the channels; and (iv) a controller operably coupled to the detector, wherein the controller includes a computing device programmed to perform controller operations including: (1) operating the detector to detect the optical property of the nanosensors; and (2) detecting the analyte in the received interstitial fluid based on the detected optical property of the nanosensors.

Some embodiments of the present disclosure provide a system including: (i) a plurality of nanosensors, wherein each nanosensor includes a nanoparticle and is configured to selectively interact with an analyte present in interstitial fluid, and wherein each nanosensor is further configured to have an optical property that changes in response to interaction with the analyte; (ii) detection means, wherein the detection means are configured to optically detect the optical property of the nanosensors; (iii) a plurality of microneedles, wherein each microneedle includes (A) a first end configured to penetrate skin, (B) a second end opposite the first end, and (C) a channel that extends from a first opening proximate the first end to a second opening proximate the second end such that interstitial fluid is received into the channel via the first opening when the microneedle penetrates the skin, and wherein the nanosensors are disposed relative to the microneedles such that the microneedles direct the received interstitial fluid to the nanosensors via the channels; and (iv) controller means, wherein the controller means are configured to perform controller operations including: (1) operating the detection means to detect the optical property of the nanosensors; and (2) detecting the analyte in the received interstitial fluid based on the detected optical property of the nanosensors.

Some embodiments of the present disclosure provide a method including: (i) penetrating skin with a plurality of microneedles, wherein each microneedle includes (A) a first end configured to penetrate the skin, (B) a second end opposite the first end, and (C) a channel that extends from a first opening proximate the first end to a second opening proximate the second end; (ii) receiving interstitial fluid into the channels of the microneedles via the first openings of the microneedles; (iii) directing the received interstitial fluid to a plurality of nanosensors via the channels of the microneedles, wherein each nanosensor comprises a nanoparticle and is configured to selectively interact with an analyte present in the interstitial fluid, wherein each nanosensors is further configured to have an optical property that changes in response to interaction with the analyte; (iv) operating a detector to detect the optical property of the nanosensors; and (v) detecting the analyte in the received interstitial fluid based on the detected optical property of the nanosensors.

These as well as other aspects, advantages, and alternatives, will become apparent to those of ordinary skill in the art by reading the following detailed description, with reference where appropriate to the accompanying drawings.

DETAILED DESCRIPTION

Figure 1A:
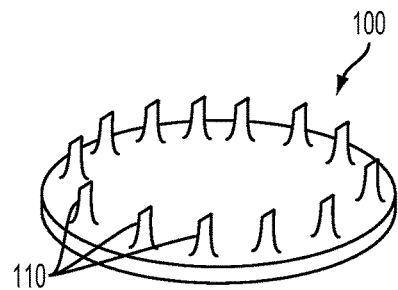
FIG. 1A is a bottom perspective view of an example device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of one or more microneedles to access a fluid in a target environment through a barrier is desired. The environment may be any living or non-living body or a portion thereof, a gel, an emulsion, a fluid conduit, a fluid reservoir, etc. For example, one of skill in the art will recognize that the embodiments disclosed herein may be used to access a target fluid (e.g., fluid of a food product, fluid within a fruit or vegetable, a pharmaceutical) within packaging, a rind, or otherwise contained within some barrier that can be penetrated by a microneedle.

I. Overview

Interstitial fluids, blood, or other fluids of a human body could be accessed through a variety of methods to allow a variety of different functions and/or applications. In some examples, a device including a plurality of microneedles could be configured to be mounted to, adhered to, or otherwise disposed proximate to skin of the human body such that the microneedles penetrate the skin, allowing access to fluids within skin tissue (e.g., interstitial fluids of the dermis) and/or beneath skin tissue (e.g., blood of cutaneous and/or subcutaneous capillaries, interstitial fluids of subcutaneous tissues). Such access could allow for extraction of fluids for detection of one or more properties (e.g., a pH, an osmolality, the concentration of one or more analytes) continuously, periodically, a single time, or according to some other sampling scheme. Conversely, such microneedle-provided access could allow one or more fluids or other agents (e.g., pharmaceuticals, electrolytes, metabolites) to be delivered into and/or through the skin.

Microneedles include a variety of hollow and solid structures configured to penetrate skin. An individual microneedle could include a first end that is sharpened, tapered, or otherwise configured to facilitate insertion into skin. The individual microneedle could additionally include second end, opposite that first end, at which the microneedle could be adhered or otherwise attached to a substrate or other structure of a device, e.g., a flexible adhesive substrate of a skin-mountable patch that includes a plurality of such microneedles. A microneedle could be solid or could have one or more channels running along the length of the microneedle (e.g., from the first end to the second end). Such a channel could extend from an opening at the first end of the microneedle to an opening at the second end of the microneedle to allow for interstitial (or other) fluid to be received into the channel when the microneedle penetrates the skin. Microneedles could be composed of metals, polymers, glasses, or other materials having specified properties (e.g., specified stiffnesses to allow for penetration of skin without buckling) relative to an application. Microneedles could have specified lengths, outer diameters, channel diameters, or other dimensions specified according to an application (e.g., to allow for sampling of interstitial fluid from specified tissues at a particular depth beneath the surface of skin).

Fluids (e.g., intracellular fluids, blood) accessed using one or more microneedles (e.g., via one or more channels of the microneedles) could be analyzed in a variety of ways. For example, the presence, concentration, or other information about one or more analytes in the fluids could be detected. Such detection could include operating a variety of sensors, including electrochemical sensors (e.g., electrodes operated to enable amperometry, voltammetry, and/or impedance measurement), optical sensors (e.g., color sensors, spectrometers, fluorescence sensors, refractive index sensors), temperature sensors, viscosity sensors, or some other sensors. For example, a plurality of nanosensors could be exposed to an interstitial fluid. The nanosensors could have an optical property (e.g., a color, a degree of fluorescence, an excitation, emission, or other spectrum) that is related to the presence, concentration, or other properties of the analyte in the fluid (e.g., the optical property could change in response to binding or other selective interaction between the analyte and the nanosensor). The optical property of the nanosensors could be detected (e.g., by illuminating the nanosensors, and detecting light responsively emitted from the nanosensors) and used to detect the analyte. The nanosensor or other analyte-sensing element(s) could be configured to selectively interact with and/or selectively respond to the analyte. Additionally or alternatively, a reagent or other element could be included and configured to selectively interact with the analyte (e.g., by producing a chemical product and/or changing the analyte in a specified way) and the interaction of the analyte with the reagent or other element could be detected. Other configurations of devices for and methods of detecting an analyte in a fluid accessed using one or more microneedles are anticipated.

One or more nanosensors or other detectors of an analyte could be exposed to a fluid accessed using one or more microneedles in a variety of ways. Interstitial (or other) fluid and/or an analyte therein received into a channel of a microneedle could be transported and/or flow through the channel and/or through some other element(s) connected to the channel due to passive forces (e.g., diffusion, capillary action between the walls of the channel and the fluid) and/or due to active elements (e.g., pumps). For example, one or more pumps could apply suction to the channels of one or more microneedles to control a flow rate of interstitial fluid through the channels. This could allow for the analyte in fluid received through the channels to be presented to nanosensors or other detectors to be continuously and/or periodically 'updated' to reflect changes in the analyte (e.g., changes in analyte concentration) in the skin. Nanosensors or other detectors could be disposed within the channels of the microneedles, or within a sampling portion, sampling chamber, reservoir, pump, microfluidic device, or other element(s) proximate to and/or connected to second ends of the microneedles (i.e., ends of the microneedles opposite the ends penetrating the skin).

Interstitial (or other) fluids beneath or within skin could be accessed using one or more microneedles. In embodiments wherein a plurality of microneedles is used to penetrate skin, each microneedle could be connected to or otherwise direct received interstitial fluid to a respective set of nanosensors or other detector(s). Alternatively, the microneedles could be connected to or otherwise direct received interstitial fluid to set of nanosensors or other detector(s) that are used and/or configured in common with all or a subset of the microneedles. Similarly, pumps, light sources, light sensors, or other elements can be configured and/or used by individual microneedles or could be used and/or configured in common with all or a subset of the microneedles. For example, each microneedle of a plurality of microneedles could provide interstitial fluid to a respective plurality of nanosensors (e.g., in a respective sensing portion, connected to a respective pump and/or associated with a respective optical detector) according to an application (e.g., to detect the concentration of the analyte at a plurality of skin locations corresponding to the plurality of microneedles). Further, more than one analyte could be detected, using microneedles in common (e.g., using respective nanosensors, sensing portions, optical detectors and/or other elements connected to common microneedles) and/or separately. For example, a first plurality of microneedles of a device could be associated with a first plurality of nanosensors or other detector(s) configured to detect a first analyte, and a second plurality of microneedles of the device could be associated with a second plurality of nanosensors or other detector(s) configured to detect a second analyte. Additional or alternative configurations of one or more microneedles to detect one or more analytes using one or more pluralities of nanosensors, other detectors, pumps, sensing portions, chambers, or other elements individually and/or in common are anticipated.

In some examples, a system as described herein could further include one or more microneedles or other elements configured to deliver a drug, fluid, or other substance (e.g., electrolytes, metabolites, vaccines) transdermally or otherwise into and/or through skin. For example, a system could include a drug reservoir containing a store an amount of a drug. The system could transdermally deliver the drug or other substance (e.g., using one or more microneedles, by introducing the drug into a gel in contact with the skin) at a controlled rate (e.g., using a pump, valve, or other flow-controlling element(s)). Such a controlled rate could be specified relative to a detected analyte; for example, a concentration of an analyte (e.g., potassium) could be detected and rate of delivery of potassium through the skin could be specified relative to the detected concentration. In another example, a concentration of glucose in the interstitial fluid could be detected, and a rate of delivery of insulin (or some other drug or substance) could be specified based on the detected concentration (e.g., to correct hyperglycemia). Analytes detected using devices or systems as described herein could include ions and/or electrolytes (e.g., chloride, potassium, calcium, sodium, particular charged proteins and/or amino acids), metabolites (e.g., glucose, urea, ammonia, creatinine), pathogens, cells, or other substances.

Such detection of analyte(s) in interstitial (or other) fluid as described herein could be performed by detectors of a device including microneedles (e.g., a skin-mountable patch including the microneedles, the detector(s), and/or other elements (e.g., batteries, controllers, electronics)) and/or by storing extracted fluids or analytes by a device including microneedles (e.g., within a reservoir of such a device) such that the stored fluids or analytes can be later analyzed and/or detected by some other system. In embodiments wherein a device including microneedles, nanosensors, detector(s), pumps, or other element(s) as described herein is configured to be mounted to skin and worn for an extended period of time (i.e., wherein the device is a wearable device), an analyte could be detected continuously, periodically, or according to some other scheme to allow for monitoring of the analyte over an extended period of time. Additionally or alternatively, some subset of elements (e.g., microneedles, nanosensors) could be included in a skin-mountable patch or other device configured to be mounted to the skin, and a reader device or other system could be configured to periodically detect the analyte in combination with the skin-mounted patch or other device. For example, a reader device could be configured to detect an optical property of the nanosensors and to detect the analyte in interstitial fluid accessed by microneedles of the skin-mountable patch or other device. This could include the reader device being removably mounted to the skin-mounted patch or other device and operating a light source and light detector of the reader device to illuminate and detect light emitted from the nanosensors, respectively. Such a reader device could additionally be configured to mount to a skin-mountable patch or other device to the skin (e.g., such that one or more microneedles penetrate the skin). Other configurations and/or operations of devices as described herein, and distributions of elements of analyte-detecting systems between skin-mountable patches, reader devices, or other components, are anticipated.

In some examples, devices as described herein may include a user interface that is configured to provide user-discernible indications (e.g., visual, audible, and/or tactile indications) of information (e.g., a detected presence, concentration, or other property of an analyte and/or a health state related thereto) sensed by the device, progress or other information related to a function of the device, or other information. In some examples, such a user interface could be disposed within a skin-mountable patch or other skin-mountable device. Additionally or alternatively, a user interface could be disposed within a reader device or other device configured to interface with (e.g., removably mount to and/or detect an optical property of nanosensors of) such a skin-mountable device. In some examples, the user interface could additionally provide a means for one or more settings of the wearable device (e.g., a sampling rate, a user information privacy setting, a drug delivery dosing) to be specified by a wearer according to the wearer's preferences. In some examples, the device may include a wireless communication interface that can transmit/receive data to/from an external device, for example, using Bluetooth, ZigBee, WiFi, and/or some other wireless communication protocol. The data transmitted by the wireless communication interface may include data indicative of a detected analyte (e.g., a presence and/or concentration of the analyte) in the blood or other fluid(s) within and/or beneath skin of the wearer. The wireless communications interface could additionally or alternatively be configured to receive data from an external system (e.g., parameters relating to the operation of the device to transdermally deliver a drug into and/or through the skin).

II. Example Microneedle Array

Devices as described herein can be configured to have one or more microneedles configured to access interstitial (or other) fluid from beneath and/or within skin to enable a variety of applications and functions including the detection of an analyte in the interstitial fluid. Such detection could include directing received interstitial fluid to nanosensors configured to have an optical property that changes in response to interaction of the nanosensors with the analyte. The analyte could be detected, using the nanosensors, by detecting the change in the optical property, e.g., by illuminating the nanosensors (e.g., with light at an excitation wavelength of a fluorophores of the nanosensors) and detecting light responsively emitted from the nanosensors (e.g., at an emission wavelength of the fluorophore of the nanosensors). Such devices could enable a variety of applications, including measuring physiological information about a wearer, indicating such measured physiological information or other information to the wearer (e.g., using a vibrator, a screen, a beeper), delivering a drug or other substance transdermally based on information about a detected analyte, or other functions.

Figure 1B:
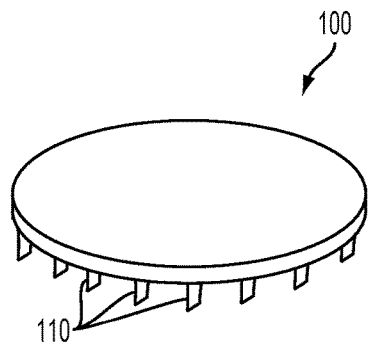
FIG. 1B is a top perspective view of the example device of FIG. 1A.

FIGS. 1A and 1B are bottom and top perspective views, respectively, of a disc-shaped wearable device 100 having a plurality of microneedles 110 arranged in a ring near the periphery of the device and protruding from one side (i.e., the bottom side) of the device. The microneedles 110 have respective first ends configured to penetrate skin and second ends, opposite the first ends, proximate to which the microneedles 110 are attached to the device 100. The microneedles 110 include respective channels extending from first openings proximate the first ends to second openings proximate the second ends such that interstitial (or other) fluid is received into the channels via the first openings when the microneedles 110 penetrate the skin. Such received interstitial fluid can be directed, via the channels, to a variety of elements of the device 110 (e.g., nanosensors, other types of sensors, sample reservoirs) according to a variety of applications. Further, the microneedles 110 could be used for other applications, for example, to deliver a drug or other substance (e.g., by directing a drug or other substance through channels of the microneedles 110, by having a coating of such a drug, by eluting or otherwise emitting such a drug from material of the microneedles 110).

The device 100 includes additional elements that are not shown, e.g., nanosensors that include nanoparticles and that have an optical property that changes based on interaction with an analyte, detector(s) configured to detect the analyte and/or to detect the optical property of the nanosensors, pumps or other microfluidic elements (e.g., valves) configured to control a flow of interstitial fluid and/or drug through the microneedles 110, electronics configured to operate detectors, pumps, or other elements of the device 100 and to enable applications and/or functions of the device 100, a rechargeable battery configured to power the device 100, or other components. Such components configured to allow detection of the analyte could be disposed on or within the device 100 or could be disposed on or within a reader device or some other system configured to interact with (e.g., to removably mount to) the device 100 when the device is mounted to skin and/or the microneedles 110 penetrate skin.

The disc-shaped housing of the device 110 is intended as a non-limiting example; the shape of a housing or other element(s) of such a device could have different shapes according to an application. The device 100 could be wholly or partially flexible (e.g., composed of flexible materials and/or of materials sufficiently thin to exhibit flexibility as part of the device 100) such that the device 100 could be conformally mounted to skin. For example, the device 100 could include one or more layers of a flexible polymer, metal, or other material, a fabric or textile. Alternatively, the device 110 could be rigid. The device 100 could be configured to be mounted to skin (i.e., could comprise a skin-mountable patch or otherwise wearable device) by a variety of methods and/or means. For example, the device 100 could be configured to be mounted to skin by an adhesive, by friction between the microneedles 110 and skin penetrated by the microneedles 110, by being attached to a body part using a mount (e.g., by being mounted to skin of a wrist or other protruding body part by a strap configured to encircle a part of a body including the skin), by including one or more barbs (e.g., barbs disposed on the microneedles 110), or by some other means.

A housing of the device 100 could be configured to be water-resistant and/or water-proof. That is, the housing could be configured to include sealants, adhesives, gaskets, welds, press-fitted seams, and/or other joints and/or could be formed from a single piece of substantially impermeable material such that the housing is resistant to water entering an internal volume or volumes of the housing (except via the microneedles 110, according to an application) when the housing is exposed to water. The housing could further be water-proof, i.e., resistant to water entering an internal volume or volumes of the housing (except via the microneedles 110, according to an application) when the housing is submerged in water. For example, the housing could be water-proof to a depth of 1 meter, i.e., configured to resist water entering an internal volume or volumes of the housing (except via the microneedles 110, according to an application) when the housing is submerged to a depth of 1 meter. Further, the interface between the housing and other elements of the device 110 (e.g., elements of a sensor, buttons, user interface elements, electrical contacts, the microneedles 110) protruding from, embedded in the surface of, or otherwise interrupting the material of the housing could be configured such that the combination of the housing and the other elements of the device 100 is water-resistant and/or water-proof. In some examples, one or more particular elements of the device 100 (e.g., an electronics module containing electronics configured to, e.g., detect an optical property of nanosensors) could be water-proof and/or water-resistant.

Note that the number of microneedles 110, their arrangement on the device, and other aspects of the configuration of the microneedles 110 are intended as a non-limiting illustrative example. More or fewer microneedles could be disposed on a similarly or differently shaped device according to an application. In some examples, a one- two-dimensional array of microneedles could be disposed on a device to enable sampling of interstitial tissues across an area of tissue, to ensure that at least one microneedle is able to receive interstitial fluids, to ensure that interstitial fluids are able to be received from regions of skin proximate to a particular target (e.g., from regions proximate to a blood vessel), or according to some other application. For example, a regularly- or otherwise-spaced array of microneedles could be configured to allow the determination of the distribution or other properties of one or more analytes across an area of skin by using each microneedle of the array to detect the analyte in a corresponding particular region of skin. Other configurations and application of arrays of microneedles as described herein are anticipated.

The device 100 could include one or more detectors and/or sensors configured to detect one or more properties of skin, of a wearer, and/or of an analyte in interstitial or other fluid(s) received from beneath and/or within skin via the microneedles 110. Such sensors and/or detectors could include one or more photodetectors (e.g., light sensors, IR sensors, UV sensors), electric field sensors, magnetic field sensors, electromagnetic energy sensors, temperature sensors, electric current sensors, electric potential sensor, acoustical sensors, force transducers, accelerometers, electrodes, or some other sensors or combination(s) of sensors. Such sensors and/or detectors could include one or more light emitters, IR emitters, electromagnetic energy emitters, heaters, vibrators, acoustical energy emitters, force transducers, or some other energy emitters. Such sensors and/or detectors could be configured to operate in direct contact with skin (e.g., configured to include a heat- or electricity-conducting probe or other element in physical contact with the skin to facilitate detection of one or more properties of the skin). Additionally or alternatively, Such sensors and/or detectors could be configured to indirectly (i.e., without directly contacting skin) detect information about the skin or some other element or elements of a human body (e.g., to detect electromagnetic, optical, acoustical, or other fields and/or energies emitted, reflected, scattered and/or generated by elements of the skin and/or body and received by the sensors and/or detectors). In particular, the sensors and/or detectors of the device could include a plurality of nanosensors configured to change an optical property in response to interaction with an analyte in interstitial tissue received via the microneedles 110 and could further include one or more detectors configured to detect the optical state of the nanosensors and thus to detect the analyte in the interstitial fluid.

Additionally or alternatively, the device 100 could be configured to detect analytes in interstitial fluid(s) and/or to perform some other functions in combination with a reader device or some other system configured to interact with the device 100 to allow such functionality. For example, the device 100 could include the microneedles 110 and a plurality of nanosensors. The microneedles 110 and/or other elements of the deice 100 (e.g., microfluidic channels, pumps, valves) could be configured to direct interstitial (or other) fluid from skin penetrated by the microneedles 110 to the nanosensors. The reader device could include a detector configured to detect an optical or other property of the nanosensors related to the analyte to allow detection of the analyte. This could include the reader device being removably mounted to the device 100 when the device is mounted to skin and/or the microneedles 110 penetrate the skin. Such removable mounting or other operation(s) of the reader device relative to the device 100 could allow for other operation(s) of the device 100, e.g., operation of other sensors disposed in the device, operation of pumps, valves, or other microfluidic elements of the device 100, or other operations.

Such operation of elements of the device 100 by a reader device could include one or more electrical contacts and/or connectors of the device 100 and/or reader device being removably or otherwise connected. Additionally or alternatively, operation of elements of the device 100 by a reader device could include the reader device exerting a magnetic field, an electric field, an acoustic field, an optical and/or electromagnetic field, or some other energy toward the device 100. For example, the reader device could emit a beam of light toward elements of a microfluidic pump of the device 100 to effect a fluid flow (e.g., a flow of interstitial fluid through the microneedles 110) on or within the device 100.

Figure 1C:
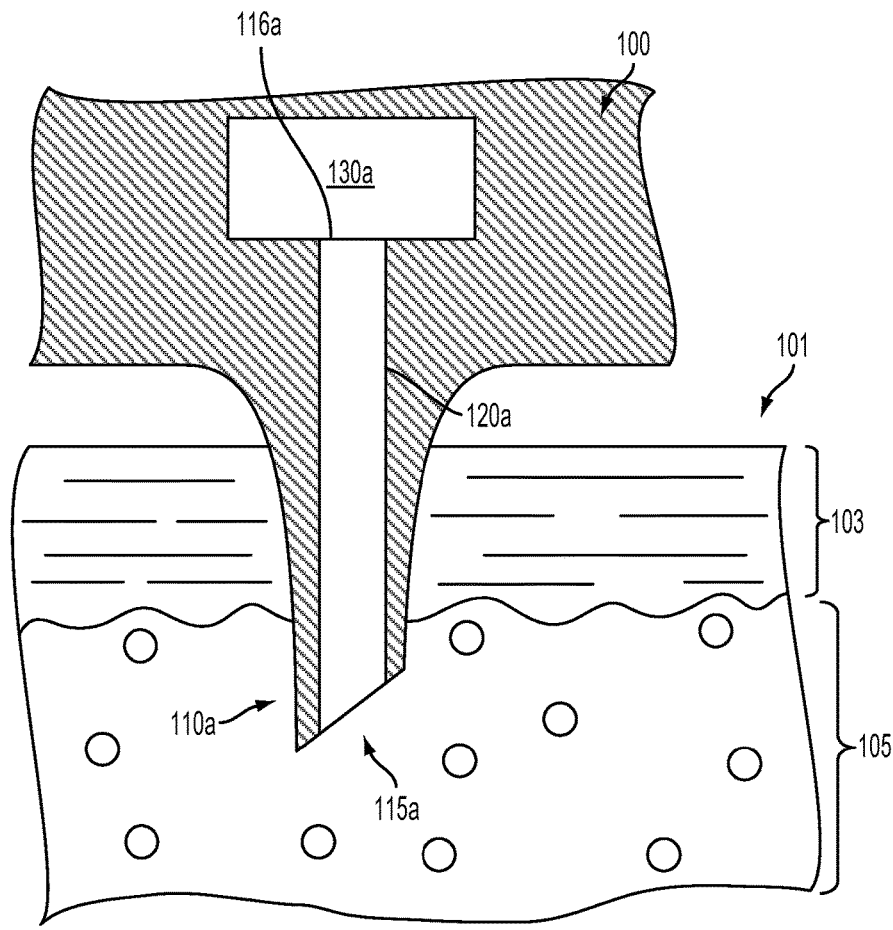
FIG. 1C is a cross-sectional schematic view of a particular microneedle of the example device of FIGS. 1A and 1B when the particular microneedle penetrates skin.

FIG. 1C is a partial cross-sectional view through a portion of skin 101 illustrating a particular microneedle 110a of the plurality of microneedles 110 that penetrates the skin 110. The skin 101 includes a superficial epidermis 103 and an underlying dermis 105. The microneedle 110a include a channel 120a extending from a first opening 115a proximate a first end of the microneedle 110a (the first end of the microneedle 110a is configured to penetrate the skin 101) to a second opening 116a proximate a second end of the microneedle 110. As shown, the microneedle 110a extends into the dermis 105. In this position, interstitial fluid from the dermis 105 can be received into the channel 120a through the first opening 115a.

The channel 120a is connected, via the second opening 116a, to a payload 130a of the device 100. In some examples, the microneedle 110a may direct interstitial fluid received into the channel 120a via the first opening 115 to the payload 130a. In some examples, the microneedle 110a may direct drugs, fluids, other substances, and/or suction from the payload 130a to the channel 120a and from the channel 120a into the dermis 105 through the first opening 115a.

The epidermis 103 is a generally impermeable or minimally permeable layer. The dermis 105 is a more permeable layer that includes vasculature, nerves, and other components. Further, due to perfusion and/or circulation provided by vasculature in the dermis 105, content of the dermis 105 (e.g., interstitial fluid) can have one or more properties related to the blood of a person or to some other health state of the person. Conversely, drugs or other substances introduced into the dermis can be transported into the circulation or other regions of the body of the person.

As shown in FIG. 1C, the microneedle 110a penetrates the skin 101 such that the first opening 115a is within the dermis 105. However, other layers and/or regions of the skin 101 or other tissues of a person could be accessed by microneedles. A length or other properties of the microneedle 110a could be specified such that the first opening 115a or other aspects of the microneedle 110a are likely to be disposed within or proximate to a specified target region or layer of the skin or other tissue when the microneedle 110a penetrates the skin 101 or according to some other application. For example, a length of the microneedle 110a could be less than or equal to approximately 1 millimeter. Further, the outer diameter of the microneedle 110a, an inner diameter of the channel 120a, or other properties of the microneedle 110a and/or device 100 could be specified to allow some application. For example, such properties could be specified, related to a viscosity, density, osmolality, or other properties of a target fluid (e.g., blood, interstitial fluid) or components thereof to allow receiving such fluids via the first opening 115a and/or direction of such fluids to a payload 130a or to some other element(s) (e.g., nanosensors in the payload 130a, nanosensors disposed on or within the microneedle 110a) of the device 100 according to an application. Further, properties of the microneedle 110a could be specified to minimize discomfort during use and/or mounting/insertion (e.g., to minimize effects of the microneedle 110a on nerves within the skin 101) of the device 100. In some examples, an outer diameter of the microneedle 100a could be approximately 100 micrometers.

The microneedle 110a could be composed of one or more materials according to an application. Generally, the microneedle 110a is composed of a stiff material such that the microneedle 110a can penetrate skin (e.g., 101) without buckling, bending, deforming, substantially reducing the diameter of and/or pinching the channel 120a, or otherwise being damaged and/or hindering the reception of interstitial (or other fluid) into the channel 120a via the first opening 115a and/or the direction of such fluid or other substances (e.g., drugs) through the channel 120a. The microneedle 110a could be composed of metals (e.g., stainless steel, platinum), polymers (e.g., polymethyl methacrylate (PMMA), polycaprolactone (PCL)), or other stiff materials. Further, the material(s) of the microneedle 110a could be chosen to have some other specified properties. In some examples, nanosensors could be disposed on or within the microneedle 110a and exposed to an analyte in the skin 101 and an optical property of the nanosensors (e.g., a color, a fluorescence amplitude) could be detected to allow for detection of the analyte. In such examples, a material of the microneedle 110a could be chosen to have one or more optical properties (e.g., transparency, clarity, optical bandwidth, refractive index) to allow for detection of the optical property of the nanosensors by elements (e.g., light sources, light sensors) of the device 100. For example, the microneedle 110a could include PMMA, glass, and/or PCL. Further, in such examples, the geometry and/or dimensions of the microneedle 110a could be specified to allow detection of the optical property of the nanosensors (e.g., the microneedle 110a could be configured to act as an optical waveguide). In some examples, the microneedle 110a could be composed of a bio-absorbable (e.g., PCL, polylactic acid (PLA)) and/or biocompatible (e.g., PMMA, platinum, stainless steel) material and/or could have a coating of a biocompatible material (e.g., polyamides and/or polyurethanes).

The microneedles 110 could be formed by a variety of processes. The microneedles 110 could be formed by injection or other varieties of molding, photolithography, machining, or some other method or combination of methods. In some examples, the microneedles 110 and one or more other elements of the device 100 (e.g., a housing, one or more microfluidic channels, pumps, valves, or other elements) could be formed with the microneedles 110. Additionally or alternatively, one or more microneedles 110 could be formed independently and assembled into some other element(s) of the device 100. For example, the microneedles 110 could be formed and then attached (e.g., adhered to, bonded, pressfitted into) to a housing or other element(s) of the device 100.

The channel 120a and/or other elements of the device 100 and/or microneedle 110a could include a coating configured to control the flow of interstitial or other fluids into the channel 120a via the first opening 115a and/or through the channel 120a into other elements of the device 100 (e.g., elements of the payload 130a). For example, such elements could include a hydrophilic coating to enable aqueous solutions to more easily wet surfaces and/or flow within coated channels, tubes, valves, or other microfluidic elements (e.g., 120a). Such hydrophilic coatings and/or substances could include polyethylene glycol (PEG).

The payload 130a could include a variety of elements. The payload 130a could include one or more chambers, channels, reservoirs, valves, pumps, or other microfluidic elements configured to receive, channel, mix, or otherwise interact with interstitial (or other fluid) received into the channel 120a via the first opening 115a when the microneedle 110a penetrates the skin 101 and directed to the payload 130a via the channel 120a. The payload 130a could include a pump and/or valve configured control a flow rate of fluid through the channel 120a. The payload 130a could include one or more reservoirs configured to store received interstitial fluid, e.g., for later analysis and/or for some other application. The payload 130a could include a drug or other substance (e.g., stored in a reservoir) and could be configured to deliver such drug or other substance into and/or through the skin 101 using the microneedle 110a. Delivery of drugs and/or other substances could be performed base on detected information about the skin, analytes in interstitial fluid of the skin, or some other information. The payload 130a could include one or more sensors configured to detect one or more properties of a received interstitial fluid (e.g., to detect an analyte in the fluid). Additional or alternative contents and/or configurations of the payload 130a are anticipated.

The payload 130a could include one or more components configured to detect one or more properties (e.g., a presence, a concentration, a state) of one or more analytes in interstitial fluid received via the channel 120a. Such detection could include operating a variety of sensors, including electrochemical sensors (e.g., electrodes operated to enable amperometry, voltammetry, and/or impedance measurement), optical sensors (e.g., color sensors, spectrometers, fluorescence sensors, refractive index sensors), temperature sensors, viscosity sensors, or some other sensors. For example, a plurality of nanosensors could be exposed to an interstitial fluid. The nanosensors could have an optical property (e.g., a color, a degree of fluorescence, an excitation, emission, or other spectrum) that is related to the presence, concentration, or other properties of the analyte in the fluid (e.g., the optical property could change in response to binding or other selective interaction between the analyte and the nanosensor). The optical property of the nanosensors could be detected (e.g., by illuminating the nanosensors, and detecting light responsively emitted from the nanosensors) and used to detect the analyte. The nanosensor or other analyte-sensing element(s) could be configured to selectively interact with and/or selectively respond to the analyte. Additionally or alternatively, a reagent or other element could be included and configured to selectively interact with the analyte (e.g., by producing a chemical product and/or changing the analyte in a specified way) and the interaction of the analyte with the reagent or other element could be detected. Other configurations and/or operations of the payload 130a to detect an analyte in a fluid accessed using the microneedle 110a are anticipated.

In some examples, the device 100 could include a plurality of nanosensors. Such nanosensors could include nanoparticles that have one or more chemicals, proteins, or other elements incorporated within and/or adsorbed onto the surface of the nanoparticles. Such nanosensors could include analyte-selective agents (e.g., ionophores, receptors, proteins, ion channels) configured to selectively interact with a particular analyte in interstitial (or other) fluid. Such nanosensors could additionally include fluorophores, chromophores, or other components having an optical property that is changed, directly or indirectly, by interaction of the nanosensor with the analyte. In some examples, interaction with the analyte (e.g., binding with the analyte) could cause a quenching of a fluorophore, changing of a color of a chromophore moiety, or some other optical effect due to modification of the fluorophore or chromophore, positioning of a quencher or other element(s) proximate to the fluorophore or chromophore (e.g., in a manner similar to Forster resonance energy transfer (FRET) imaging).

Additionally or alternatively, interaction with the analyte could cause a change in local properties (e.g., pH, osmolality, charge, voltage, hydrophobicity) of the environment of the fluorophore or chromophore. For example, the analyte could be selectively altered by and/or selectively cause the production of a chemical product (e.g., hydrogen peroxide) by a protein of the nanosensor, and the fluorophore or chromophore could have a property (e.g., a fluorescent property, a fluorescence amplitude, a color) that is dependent upon the presence and/or concentration of the altered analyte and/or chemical product. In another example, the analyte could be an ion, and the nanosensor could include an ionophore. The nanosensor could further include a linking agent that changes a local pH in response to the ionophore selectively interacting with the analyte. The nanosensor could further include a pH-sensitive fluorophore having a fluorescent property that is dependent upon the local pH. A fluorescent or other optical property of a fluorophore of a nanosensor could be detected (e.g., by a detector of the payload 130a and/or by a detector in a reader device) by emitting light at an excitation wavelength of the fluorophore (e.g., using an LED, a laser, or some other light source and/or light filters or other optical elements) and receiving responsively emitted light from the fluorophore at an emission wavelength of the fluorophore (e.g., using a phototransistor, photodiode, photoresistor, camera, CCD, active pixel sensor, or other light-sensitive element(s) and/or light filters or other optical elements). Other methods of detecting a fluorescent or other optical property of a nanosensor are anticipated.

The rate of flow of received interstitial fluid, drugs, or other substances through the channel 120a and/or through some other element(s) of the device 100 could be controlled and/or specified in a variety of ways. In some examples, the device 100 (and/or a reader device or other system configured to operate in combination with the device 100) could include one or more active elements, e.g., pumps, valves, or other devices, configured to use provided electrical, optical, mechanical, or other form of energy to induce a flow within a fluid and/or the create a pressure differential in order to control flow of interstitial fluid or other substances. Additionally or alternatively, such a flow could be controlled and/or specified by configuring one or more elements of the device 110 such that the flow occurs without the addition of an energy by the device, e.g., by taking advantage of a pressure differential between an environment within the skin (e.g., an environment proximate to the first opening 115a) and another environment accessible by the device 100 (e.g., an ambient environment around the device, a positively or negatively pressurized volume or reservoir within the device 100), controlling and/or specifying properties of the channel 120a or other elements of the device to control a flow (e.g., tailoring a hydrophobicity, diameter, or other properties of the channel 120a and/or payload 130a such that flow of interstitial fluid through the channel 120a is energetically preferred).

Elements of the device 100 configured to actively control fluid flows could include a variety of pumps, valves, electrowetting surfaces, or other actuators or elements. Pumps could include centrifugal, peristaltic, microfluidic, or other varieties of pumps. Pumps could be actuated by motors, piezoelectric elements, electrowetting surfaces, optically actuated elements, or other types of elements. Further, such pumps could be included in a reader device or other system configured to operate in combination with the device 100. For example, a reader device could include a vacuum pump connected to a vacuum interface that include a seal, a connector, or some other element(s) configured to couple a vacuum to one or more elements (e.g., the channel 120a) of the device 100. Valves could include fluidic gates or switches actuated by mechanical flaps (actuated, e.g., by piezoelectric elements), controlled electrowetting electrodes or regions, one or more electrodes disposed outside of a gating or switching element and configured to generate an electrical field to control the behavior of fluids within the gating or switching elements, or other fluid gating or switching elements.

Element(s) of the device configured to allow and/or control a fluid flow within the device passively could be configured to do so once, for a limited period of time, and/or for a limited amount (e.g., volume) of flow. For example, the payload 130a could include a hydrophilic reservoir connected to the channel 120a and configured to attract and/or draw an amount of interstitial (or other fluid) through the channel 120a into the hydrophilic reservoir. Such a passive system could allow for detection of properties of the interstitial (or other) fluid (e.g., the concentration or presence of an analyte) in the skin 101 at a point in time relative to the insertion of the microneedle 110a (i.e., a time when the fluid initially flows into the hydrophilic reservoir).

Controlling a flow of fluid through the channel 120a (e.g., using a pump or other element(s)) could allow for detection of changes in properties of the interstitial (or other) fluid of the skin 101 over time. That is, an amount of interstitial fluid could be received into the first opening 115a due to a controlled fluid flow through the channel 120a. As a result, a property of the amount of fluid (e.g., the presence or concentration of an analyte) could be detected and inferred to correspond to the property of the interstitial fluid and/or skin 101 at the time the amount of fluid is received into the first opening 115a. By controlling the flow through the channel 120a to provide a continuous (or otherwise specified) flow rate, changes in properties of the interstitial fluid and/or skin over time can be detected.

In some examples, a continuous or otherwise specified flow rate of fluid through the channel 120a could be provided by passive means. For example, a path could be provided between the channel 120a at the second end of the microneedle 110a and an ambient pressure of the atmosphere in the environment of the device 100. This ambient pressure could be less than a pressure of fluid within the skin 101 (i.e., there could exist a pressure differential between the tissues proximate the first opening 115a and the environment) such that a fluid flow through the channel 120a could be driven by the pressure difference. This flow could be controlled by one or more specified fluid resistances of elements of the device 100 (e.g., a fluid resistance of the channel 120a due to a diameter of the channel 120a, a length of the channel 120a, a property of coating of the channel 120a, or some other properties of the channel 120a).

Additionally, this flow could be controlled by one or more valves or other actuated elements of the device 100. In some examples, such valves could be operated to control an effective resistance of the valves to control a flow rate of fluid. Additionally or alternatively, the valves could be operated to switch between closed and open states at a specified frequency, duty cycle, or according to some other specified scheme to control a flow rate of fluid. In some examples, a valve could be operated in combination with a hydrophilic reservoir or other element(s) configured to control a fluid flow within the device once, for a limited period of time, and/or for a limited amount (e.g., volume) of flow to control a timing of the operation of such a hydrophilic reservoir or other element(s). In such examples, a plurality of such hydrophilic reservoir or other element(s), valves, and/or other elements could be operated in combination with one or more microneedles 110 to allow for detection of properties of the interstitial (or other) fluid in the skin 101 at a plurality of points in time relative to the activation of the valves.

A flow rate of interstitial fluid through the channel 120a could be controlled in a variety of ways related to sampling of the interstitial fluid for a variety of applications, e.g., for the detection of an analyte in interstitial fluid of the skin 101. In some examples, a continuous flow rate could be provided to allow for continuous sampling. In some examples, the flow rate could be controlled to provide a specified flow rate during a plurality of periods of time to allow sampling during the plurality of periods of time. This periodic flow could be controlled to reduce a power consumption (e.g., of a pump) of the device 100. In some examples, a flow rate could be controlled to substantially stop flowing during a sampling time or period to allow for an improved measurement of a property of a received interstitial (or other) fluid (e.g., to allow for a longer light integration period for a particular sample).

Note that configurations and/or operations of devices as described herein to control fluid flows (e.g., fluid flows through the channel 120a) could be applied to transdermally deliver a drug, fluid, or other substance using the device 100. For example, a flow rate of a drug through the channel 120a into the skin 101 could be controlled using a pump and/or valve. In another example, a drug could be stored in a pressurized reservoir, and a valve could be opened or closed to control the flow of the drug through the channel 120a. Other configurations and operations of the device 100 to transdermally deliver a drug, fluid, or other substance (e.g., a vaccine) into the skin are anticipated. Further, a rate of delivery of drug or some other property of transdermal drug or other substance delivery could be controlled based on a detected property of an interstitial (or other) fluid (e.g., presence and/or concentration of an analyte therein), the skin, and/or Devices (e.g., 100) and other embodiments as described herein can include a variety of components configured in a variety of ways. Devices described herein could include electronics including a variety of different components configured in a variety of ways to enable applications of the wearable device. The electronics could include controllers, amplifiers, switches, pump controllers, valve controllers, motors, piezo elements, electrowetting electrodes, electrochemical electrodes, light sources, light sensors, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors and/or components of sensors to detect a property of interstitial (or other) fluid received by the device. The controller could include a processor configured to execute computer-readable instructions (e.g., program instructions stored in data storage of the wearable device) to enable applications of the wearable device. The electronics can include additional or alternative components according to an application of the device (e.g., 100).

Devices (e.g., 100) and/or reader devices or other systems configured to operate in combination therewith as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the device, to determine some property of the device and/or of the wearer of the device (e.g., a presence and/or concentration of an analyte), or to provide some other functionality or application to the wearer and/or user. As one example, the user interface could be operated to indicate the presence of an analyte in interstitial fluid accessed by the device through and/or from skin of a wearer. As another example, the user interface of a reader device could be operated to indicate a force and/or displacement applied to a device to penetrate skin using a plurality of microneedles, e.g., to inform the mounting of the device such that the microneedles access interstitial fluid of a specified tissue in or beneath the skin and/or at a specified depth beneath the surface of the skin. The user interface could be configured to provide one or more recommendations or alerts generated either from a remote server or other remote computing device, or from a processor within the device. The alerts could be related to a health state of a wearer determined based on a detected property of interstitial fluid received by the device (e.g., a presence or concentration of an analyte in the interstitial fluid). Other indicated information, changes in operation of the device, or other functions and applications of a user interface are anticipated.

Note that the embodiments illustrated herein (e.g., in FIGS. 1A-C, 2, 3A-C, 4A-C, 5, and 6 are illustrative examples and not meant to be limiting. Alternative embodiments, including more or fewer components in alternative configurations are anticipated. A device could be configured as a wearable device, a skin-mountable patch, or according to some other form factor or application. A device could be configured to perform a variety of functions and to enable a variety of applications. Devices could be configured to operate in concert with other devices or systems; for example, devices could include a wireless communication interface configured to transmit data indicative of one or more properties of the body of a wearer (e.g., detected analytes in interstitial fluid) of the device. Other embodiments, operations, configurations, and applications of a device as described herein are anticipated.

III. Example Microneedle Devices

Figure 2:
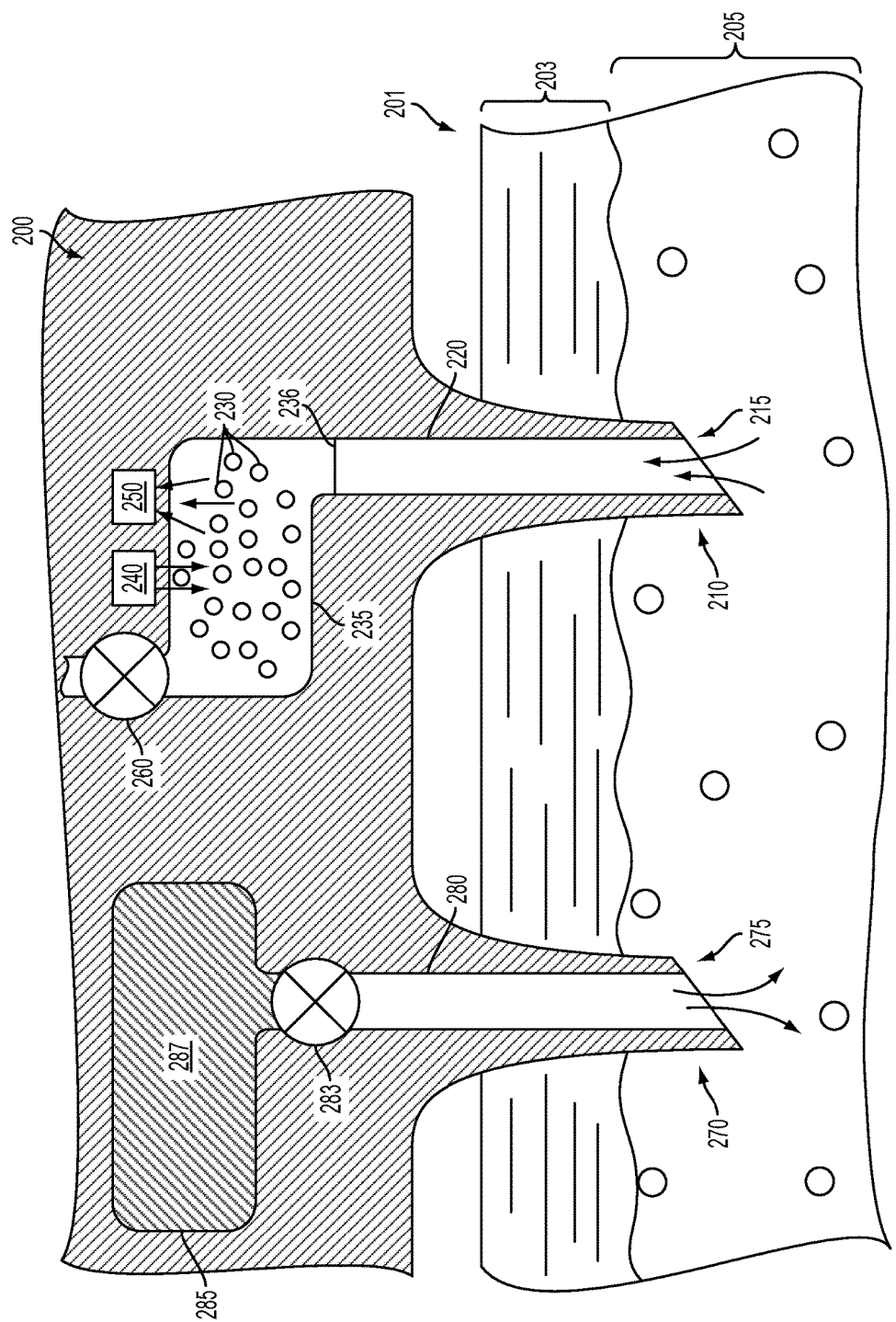
FIG. 2 is a cross-sectional schematic view of microneedles of an example device when the microneedles penetrate skin.

FIG. 2 is a partial cross-sectional view through a portion of skin 201 illustrating a first 210 and second 270 microneedles of a device 200 that penetrate skin 201. The microneedles 210, 270 include respective channels 220, 280 extending from respective first openings 215, 275 at respective first ends of the microneedles 210, 270 (the first ends are configured to penetrate the skin 201) toward respective second ends of the microneedles 210, 270. The first channel 220 is connected to a sensing portion 235 of the device 200 (e.g., via a second opening 236 proximate the second end of the microneedle 210). The sensing portion 235 contains a plurality of nanosensors 230 and can receive interstitial fluid that entered the channel 210 via the first opening 215 such that the nanosensors 230 are exposed to the received interstitial fluid. A pump 260 can also be connected to the sensing portion 235. A light source 240 is configured to illuminate the nanosensors 230 and a light sensor 250 is configured to receive light emitted from the nanosensors (e.g., in response to being illuminated by the light source 240). The second channel 280 is connected, via a pump 283, to a reservoir 285 that stores an amount of a drug 287 and is configured to transdermally deliver the drug 285 into the skin 201. The skin 201 includes a superficial epidermis 103 and an underlying dermis 105.

The nanosensors 230 include nanoparticles (e.g., particles having one or more dimensions at the nano-scale) and are configured to selectively interact an analyte present in interstitial fluid and further configured to have an optical property that changes in response to interaction with the analyte. In a particular example, wherein the analyte is an ion, this includes the nanosensors 230 including an ionophore configured to selectively interact with the analyte. The ionophore could include a crown ether, a cryptand, a calixarene, a protein or complex of proteins (e.g., valinomycin, salinomycin gramicidin A), or some other element(s) or combination of elements selected and/or configured to selectively interact with a particular target ion and/or set of target ions. The nanosensors 230 could additionally include a pH-sensitive fluorophore (e.g., fluorescein) having a fluorescent property (e.g., a fluorescence amplitude, a fluorescence lifetime, an excitation spectrum, an emission spectrum) that is dependent upon the local pH (i.e., the pH of a local to the fluorophore and/or to a particular nanosensor that includes a particular fluorophore). The nanosensors further include a linking agent configured to change the local pH in response to the ionophore selectively interacting with the analyte.

In some examples, the linking agent could be a part of the ionophore (e.g., a moiety of a protein or protein complex that includes the ionophore) such that a conformation change or other activity of the ionophore/linking agent causes the change in the local pH. In some examples, the linking agent could be configured to balance a charge of the nanosensors 230 and/or of some elements of the nanosensor 230 (e.g., of a complex of one or more ionophores and one or more linking agents) such that selective interaction (e.g., binding) of a charged analyte (i.e., ion) with the ionophore causes the release or capture of one or more protons by the linking agent, resulting in a change in the local pH. Additionally or alternatively, the nanosensors 230 could include one or more pH-sensitive chromophores (e.g., azolitmin, bromocresol purple, bromocresol blue, phenol red, naptholphthalein) having an optical property (e.g., a color) that is related to the local pH.

In some examples, ionophores, linking agents, fluorophores, chromophores, receptors, proteins, or other elements of the nanosensors 230 could be bound and/or adsorbed to the surface of nanoparticles of the nanosensors 230. Additionally or alternatively, ionophores, linking agents, fluorophores, chromophores, receptors, proteins, or other elements of the nanosensors 230 could be bound within and/or absorbed into the material of and/or an internal volume of nanoparticles of the nanosensors 230. In some examples, the nanoparticles could be micelles, liposomes, shells, or other ordered structures, and one or more of the elements of the nanosensors 230 could be embedded within and/or through a wall of the nanoparticles. Such embedding could allow for one or more functions of the nanosensors 230. For example, the ionophore and linking agent could comprise a transmembrane ion pump that removes a proton from the interior of the nanoparticle in response to interaction with an analyte ion (which the transmembrane ion pump may additionally sequester within the nanoparticle).

Additional or alternative configurations of nanosensors 230 are anticipated. In some examples, interaction with the analyte (e.g., binding with the analyte) could cause a quenching of a fluorophore, changing of a color of a chromophore moiety, or some other optical effect due to modification of the fluorophore or chromophore, positioning of a quencher or other element(s) proximate to the fluorophore or chromophore (e.g., in a manner similar to Forster resonance energy transfer (FRET) imaging), or some other mechanism or activity of the nanosensors 230.

Detecting an optical property of the nanosensors 230 includes illuminating the nanosensors 230 using the light source 240 and detecting light responsively emitted from the nanosensors 230 using the light sensor 250. Together, the light source 240 and light sensor 250 form a detector configured to detect the optical property of the nanosensors 230 that changes in response to interaction with the analyte. Properties of the light emitted by the light sensors 240 and/or of the detected by the light sensor 250 of light emitted from the nanosensors 230 could be specified relative to properties of the nanosensors 230. For example, the optical property of the nanosensors 230 could be a fluorescence intensity that is related to interaction of the nanosensors with the analyte. In such an example, the light source 240 could emit light at an excitation wavelength of the fluorophore and the light sensor 250 could detect the amplitude of light received at an emission wavelength of the fluorophore. In examples wherein the optical property is a color of the nanosensors 230 (e.g., the nanosensors 230 include a chromophore having a color that changes related to interaction with the analyte), the light source 240 could emit light at a range of different wavelengths (e.g., could emit a white light) and the light sensor 250 could detect light at two more different specified wavelengths to enable determination and/or detection of the color of the chromophore. Additionally or alternatively, the light source 240 could emit light at two or more specified wavelengths, and the light sensor 250 could detect the amplitude of light responsively emitted from the nanosensors 230 to enable determination and/or detection of the color of the chromophore.

Generally, detection of an optical property of the nanosensors 230 can include operating the light source 240 to emit light at one or more specified wavelengths, across a range of wavelengths, and/or according to a specified spectrum. Further, detection of an optical property of the nanosensors 230 can include operating the light sensor 240 to detect the color, amplitude, spectrum, polarization, phase, coherence, or other properties of light responsively emitted from the nanosensors 230 at one or more specified wavelengths, across a range of wavelengths, and/or according to a specified spectrum. These operations can allow for the detection and/or determination of an absorption spectrum, an emission spectrum, an excitation spectrum, a reflectance spectrum, some property of one or more such spectra, or some other optical property of the nanosensors 230 that is related to the interaction of the analyte with the nanosensors 230. Further, note that reference herein to 'light' (e.g., light source, light sensor, emitted light, illumination/illuminating light) refers to electromagnetic radiation at across a range of potential wavelengths, e.g., visible light, infrared radiation, and ultraviolet radiation.

Further, one or more properties of the analyte (e.g., the presence, concentration, state, or other information about the analyte) in interstitial fluid could be detected using other means. For example, the device 200 could include electrochemical sensors, viscosity sensors, spectroscopes, pH sensors, impedance sensors, temperature sensors, or some other sensors configured to detect the analyte in the interstitial fluid, or to detect some other property of the skin 201 and/or of a wearer of the device 200.

The nanosensors 230 could be disposed within the sensing portion 235 in a number of ways. In some examples, the sensing portion 235 could include a chamber within the device 200 and the nanosensors 230 could be covalently bound to, adsorbed onto, or otherwise attached to walls of the chamber. In some examples, sensing portion 235 could include a fluid-permeable matrix, such as a gel, porous material, or fluidic network, and the nanosensors 230 could be bound and/or otherwise disposed within the fluid-permeable matrix. In some examples, the nanoparticles 230 could be freely moving within the sensing portion 235. In such examples, the sensing portion 235 could include barriers to keep the nanosensors 230 within the sensing portion 235.

As shown in FIG. 2, flow of interstitial fluid through the first channel 220 is controlled by the pump 260. The pump could be a peristaltic pump, a centrifugal pump, an impedance pump, a microfluidic pump, or some other type of pump. Alternatively, a vacuum pump could be included in the device 200 and could be configured to apply a vacuum (e.g., an empty tube or further channel) to an exit port of the sensing portion 235 to cause and/or control fluid flow through the first channel 220. The pump 260 or other system configured to control the flow of fluid through the first channel 220 could additionally or alternatively include one or more valves. For example, the pump 260 could comprise a vacuum pump connected, via a valve, to the sensing portion 235. Operation of the valve could allow control of the application of a vacuum, by the vacuum pump, to the sensing portion 235, thus controlling the flow of fluid though the first channel 220.

Note that the size, shape, position relative to each other and the first microneedle 210, and other illustrated and/or described properties of the pump 260, sensing portion 235, and other elements of the device 200 are intended as non-limiting examples. As shown in FIG. 2, the sensing portion 235 (containing the nanosensors 230) is proximate to the second end of the first microneedle 210. However, set of tubing, valves, or other elements could be interposed between the channel 220 and a sensing portion or other region containing nanosensors (or other types of detectors or sensors) configured to detect an analyte. Further, the sensing portion 235 could be connected to the channels of multiple microneedles to allow for detection of the analyte in interstitial fluid extraction from multiple locations in the skin 201 through the multiple channels. Additionally or alternatively, the pump 260 could be connected to multiple sensing portions (each containing the same nanosensors and/or respective different pluralities of nanosensors, configured to selectively interact with respective different analytes). Further, connections between multiple microneedles (and channels thereof), multiple sensing portion, multiple pumps, and/or other elements could be controlled and/or switched by one or more valves.

Further, the sensing portion 235 could contain further pluralities of nanosensors sensitive to respective further analytes. Such further pluralities of nanosensors could have respective ionophores, linking agents, fluorophores, chromophores, or other elements according to an application. Further, the light source 240 and/or light sensor 250 could be configured and/or porated to allow for detection of a further optical property of the further nanosensors, e.g., by emitting light at a different wavelength or having some other different property and/or detecting emitted light at a different wavelength or having some other different property. For example, a first plurality of nanosensors (e.g., 230) located in the sensing portion and 235 configured to selectively interact with a first analyte could have a first excitation wavelength and a second plurality of nanosensors located in the sensing portion 235 and configured to selectively interact with a second analyte could have a second excitation wavelength, and the light source 240 could be operated to allow for substantially independent detection of the optical properties of the two pluralities of nanosensors by alternatively emitting light at the first and second wavelengths. Additionally or alternatively, a first plurality of nanosensors (e.g., 230) located in the sensing portion and 235 configured to selectively interact with a first analyte could have a first emission wavelength and a second plurality of nanosensors located in the sensing portion 235 and configured to selectively interact with a second analyte could have a second emission wavelength, and the light sensor 250 could be operated to allow for substantially independent detection of the optical properties of the two pluralities of nanosensors by alternatively detecting light emitted from the sensing portion 235 at the first and second wavelengths. Other methods of configuring and/or operating elements of the device 200 to detect multiple analytes using multiple pluralities of nanosensors are anticipated.

Further the device 200 could include multiple sensing portion or other structures containing nanosensors and configured to allow optical detection of nanosensors contained within the sensing portion or other structures. Such multiple sensing portions could be connected in series, in parallel, or according to some other arrangement relative to each other, to one or more microneedles and/or channels thereof, one or more pumps, or other elements of the device 200. For example, one or more microneedles could be connected to a first sensing portion containing a first plurality of nanosensors configured to selectively interact with a first analyte. A second sensing portion containing a second plurality of nanosensors configured to selectively interact with a second analyte could additionally be connected to the first sensing portion such that interstitial fluid received through channels of the one or more microneedles is directed to the second sensing portion (and the second plurality of nanosensors therein) through the first sensing portion. Optical properties of the first and second pluralities of nanosensors could be detected using respective first and second light sources and light sensors. Additionally or alternatively, a single light source and/or light sensor could be used to detect the optical properties of the first and second pluralities of nanosensors. For example, a single light source could be configured to illuminate both pluralities of nanosensors, and first and second light sensors could be configured to receive light responsively emitted by the first and second pluralities of nanosensors, respectively.

The second microneedle 270 and channel 280 are configured to transdermally deliver the drug 287 stored in the drug reservoir 285. As illustrated in FIG. 2, a flow rate of the drug and/or a carrier fluid containing the drug can be controlled by a pump 283. The pump 283 could be any kind or configuration of pumps, valves, or other flow-control devices as described elsewhere herein. Additionally or alternatively, the reservoir 285 could contain one or more of electrolytes, metabolites, vaccines, cells, antibodies, vitamins, or other substances. The flow rate of the drug 287 could be controlled relative to a detected analyte; for example, a concentration of an analyte (e.g., potassium) could be detected and rate of delivery of potassium through the skin could be specified relative to the detected concentration. In another example, a concentration of glucose in the interstitial fluid could be detected, and a rate of delivery of insulin (or some other drug or substance) could be specified based on the detected concentration (e.g., to correct hyperglycemia). Analytes detected using devices or systems as described herein could include ions and/or electrolytes (e.g., chloride, potassium, calcium, sodium, particular charged proteins and/or amino acids), metabolites (e.g., glucose, urea, ammonia, creatinine), pathogens, cells, or other substances. Drugs or other substances transdermally delivered using the device 200 could be the same as an analyte being detected by the device (e.g., a supplement of the analyte could be introduced into the body of a wearer to increase the level of the analyte in the body to a specified level). The flow rate of the drug 287 could additionally be related to other detected properties of the body of a wearer and/or to combinations of detected properties. In some examples, a flow rate of a transdermally delivered drug could be specified based on a determined health state of a wearer (e.g., a fatigue state), where the health state is determined based on a plurality of detected analytes and/or other detected properties of the body of a wearer (e.g., based on detected creatinine levels, glucose levels, and electrolyte levels in interstitial fluid).

As illustrated in FIG. 2, the flow rate of the drug 287 through the second channel 280 is controlled by a pump 283. However, the flow rate of the drug could be controlled and/or specified through a variety of additional or alternative methods. In some examples, the drug reservoir 285 could be pressurized (e.g., by being composed of an elastic or otherwise compliant membrane or other enclosing structure and by being filled with an amount of drug 287 sufficient to place the drug reservoir 285 under sufficient tension that the pressure within the drug reservoir 285 is elevated), and the flow rate of drug 287 through the second channel 280 could be controlled by a valve being operated to switch between closed and open states at a specified frequency, duty cycle, or according to some other specified scheme to control a flow rate of fluid. Additionally or alternatively, a valve could be operated to control an effective resistance of the valve to control the flow rate of drug 287 through the second channel 280. Further alternative configurations to control and/or specify a rate of flow of the drug 287 through the second channel 280 are anticipated. Further, the device 200 could include additional means for transdermally delivering a drug (e.g., by controlling a rate at which the drug is added to a transdermal drug delivery gel or patch in contact with the skin 201).

Figure 3A:
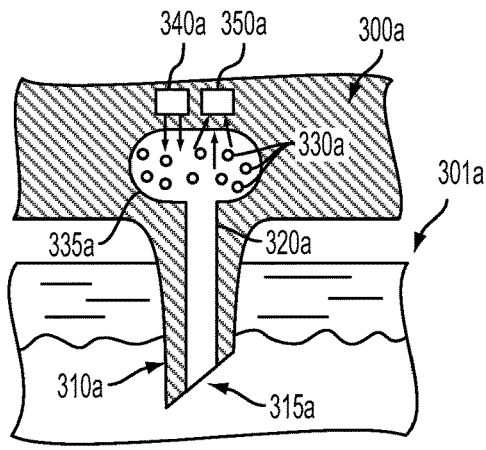
FIG. 3A is a cross-sectional schematic view of a microneedle of an example device when the microneedle penetrates skin.

Note that the example of a pump 260, sensing portion 235, and other elements associated with the first microneedle 210 and configured to allow an interstitial fluid to be delivered to the nanosensors 230 is intended as a non-limiting example. For example, element(s) of the device configured to allow and/or control a fluid flow within the device passively could be configured to do so once, for a limited period of time, and/or for a limited amount (e.g., volume) of flow. For example, FIG. 3A is a partial cross-sectional view through a portion of skin 301a illustrating a microneedle 310a of a device 300a that penetrates the skin 301a. The microneedle 310a includes a channel 320a extending from a first opening 315a at a first end of the microneedle 310a that is configured to penetrate the skin 301a. The channel 320a is connected to a sensing portion 335a that contains a plurality of nanosensors 330a and is configured to direct interstitial fluid received into the channel 310a via the first opening 315a to the nanosensors 330a in the sensing portion 335a.

The sensing portion 335a includes a hydrophilic material (e.g., has a hydrophilic coating disposed on a surface inside a chamber of the sensing portion 335a) and/or is otherwise configured to attract and/or draw an amount of interstitial (or other fluid) through the channel 320a into the sensing portion 335a. Such a passive system could allow for detection of properties of the interstitial (or other) fluid (e.g., the concentration or presence of an analyte) in the skin 301a at a point in time relative to the insertion of the microneedle 310a (i.e., a time when the fluid initially flows into the sensing portion 335a). A light source 340a is configured to illuminate the nanosensors 330a and a light sensor 350a is configured to receive light emitted from the nanosensors 330a (e.g., in response to being illuminated by the light source 340a).

The device 300a could include further elements. For example, the device 300a could include a valve configured to control the flow of fluid from the channel 320a to the sensing portion 335a. Such a valve could be operated to control a control a timing of the operation inflow of interstitial fluid into the sensing portion 335a (i.e., to control a sampling time of the sensing portion 335a). In such embodiments, a plurality of such sensing portion, pluralities of nanosensors, valves, and/or other elements could be operated in combination with the microneedles 310a to allow for detection of properties of the interstitial (or other) fluid in the skin 301a at a plurality of points in time relative to the activation of the valves.

Figure 3B:
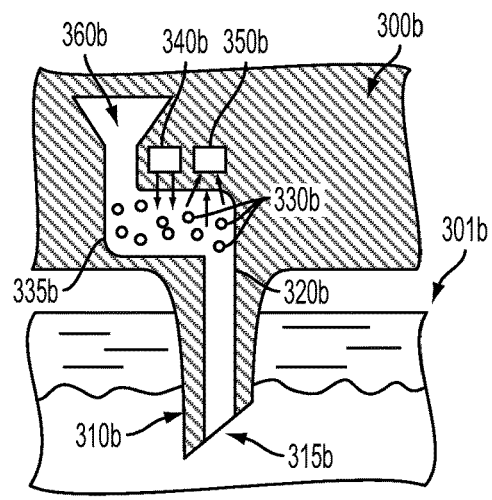
FIG. 3B is a cross-sectional schematic view of a microneedle of an example device when the microneedle penetrates skin.

In some examples, a flow rate of fluid through a microneedle could be controlled over a sustained period of time using passive means. For example, FIG. 3B is a partial cross-sectional view through a portion of skin 301b illustrating a microneedle 310b of a device 300b that penetrates the skin 301b. The microneedle 310b includes a channel 320b extending from a first opening 315b at a first end of the microneedle 310b that is configured to penetrate the skin 301b. The channel 320b is connected to a sensing portion 335b that contains a plurality of nanosensors 330b and is configured to direct interstitial fluid received into the channel 310b via the first opening 315b to the nanosensors 330b in the sensing portion 335b. An ambient port 360b provides access between the sensing portion 335b and an ambient environment of the device 300b (e.g., access to atmospheric pressure in the environment of the device). A light source 340b is configured to illuminate the nanosensors 330b and a light sensor 350b is configured to receive light emitted from the nanosensors 330b (e.g., in response to being illuminated by the light source 340b).

The device 300b provides a path between the channel 320b of the microneedle 310b at a second end of the microneedle (opposite the first end) and an ambient pressure of the atmosphere in the environment of the device (via the sensing portion 335b and the ambient port 360b). This ambient pressure could be less than a pressure of fluid (e.g., interstitial fluid) within the skin 301b (i.e., there could exist a pressure differential between the tissues proximate the first opening 515b and the environment) such that a fluid flow through the channel 320b could be driven by the pressure difference. This flow could be controlled by one or more specified fluid resistances of elements of the device 300b (e.g., a fluid resistance of the channel 320b due to a diameter of the channel 320b, a length of the channel 320b, a property of coating of the channel 320b, or some other properties of the channel 320b). Additionally or alternatively, the device 300b could include a valve configured to control the flow rate of fluid from the channel 320b to the sensing portion 335b.

Figure 3C:
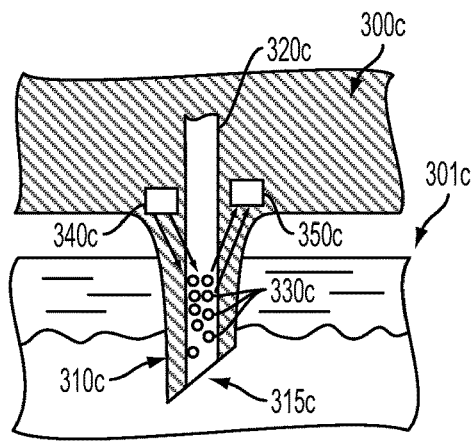
FIG. 3C is a cross-sectional schematic view of a microneedle of an example device when the microneedle penetrates skin.

Note that nanosensors of device as described herein could be location in locations other than in sensing portions or other regions or structures connected (e.g., via channels, pumps, valves, or other microfluidic elements as shown in, e.g., FIGS. 1, 2, 3A, 3B) to channels of microneedles (e.g., locations outside of the channels of microneedles and proximate to second ends of the microneedles opposite first ends of the microneedles configured to penetrate skin). In some examples, nanosensors could be disposed within channels of microneedles. For example, FIG. 3C is a partial cross-sectional view through a portion of skin 301c illustrating a microneedle 310c of a device 300c that penetrates the skin 301c. The microneedle 310c includes a channel 320c extending from a first opening 315c at a first end of the microneedle 310c that is configured to penetrate the skin 301c. The channel 320c contains a plurality of nanosensors 330c and is configured to direct interstitial fluid received into the channel 310c via the first opening 315c to the nanosensors 330c. A light source 340c is configured to illuminate the nanosensors 330c and a light sensor 350c is configured to receive light emitted from the nanosensors 330c (e.g., in response to being illuminated by the light source 340c).

The disposition of the nanosensors within the channel 310c could reduce a volume of intracellular fluid required to detect an analyte in the intercellular fluid, e.g., by reducing a volume of the channels 310c or other microfluidic elements interposed between the first opening 315c and the nanosensors 330c. The disposition of the nanosensors 330c within the channel 310c could reduce a latency between a change in the analyte in interstitial fluid in the skin 301c and the detection of a corresponding change in the analyte as detected using the nanosensors 330c for similar reasons.

The microneedle 310c could include one or more materials chosen to have one or more optical properties (e.g., transparency, clarity, optical bandwidth, refractive index) to allow for detection of the optical property of the nanosensors 330c by operation of the light source 340c and light sensor 350c of the device 300c. For example, the microneedle 310c could include PMMA, glass, and/or PCL. Further, the geometry and/or dimensions of the microneedle 310c could be specified to allow detection of the optical property of the nanosensors 330c. For example, elements of the microneedle 310c could be configured to act as an optical waveguide for light emitted by the light source 340c and/or light emitted from the nanosensors 330c.

The device 300c could include additional elements connected to the channel 320c. For example, the device could include pumps, valves, ambient ports, sensing portions, or other elements configured to perform functions and/or allow for operations according to an application. For example, a flow rate of interstitial fluid through the channel 310c could be controlled using one or more active and/or passive elements.

Devices as described herein could be operated substantially independently; that is, devices (e.g., skin-mountable patches or otherwise body mountable devices 100, 200, 300a, 300b, 300c) could include detectors, electronics, nanosensors, pumps, and/or other elements sufficient to detect an analyte in interstitial (or other) fluid beneath or within skin as accessed via one or more microneedles of the devices. Additionally or alternatively, some subset of elements (e.g., microneedles, nanosensors) could be included in a skin-mounted patch, wearable device, or other device configured to be mounted to the skin, and a reader device or other system could be configured to periodically detect the analyte in combination with the skin-mounted patch or other body-mountable device. Further, such a reader device could provide a user interface configured to indicate detected analytes and/or to receive commands to alter the operation of the reader device and/or the skin-mounted patch or other body-mountable device to detect the analyte and/or to perform some other function(s) (e.g., transdermal drug delivery).

Figure 4A:
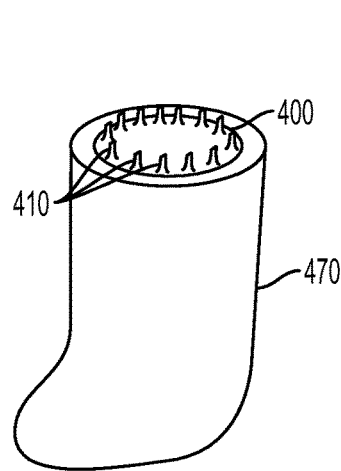
FIG. 4A is a bottom perspective view of an example skin-mountable patch removably mounted to a reader device.
Figure 4B:
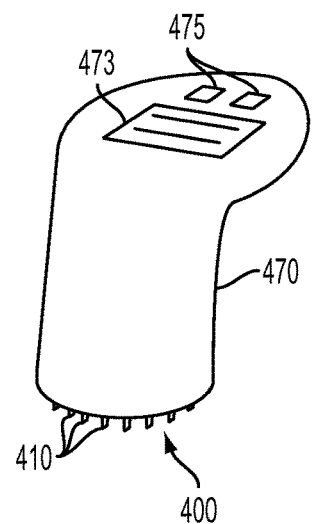
FIG. 4B is a top perspective view of the example skin-mountable patch of FIG. 4A removably mounted to the reader device of FIG. 4A.

FIGS. 4A and 4B are bottom and top perspective views, respectively, of a disc-shaped skin-mountable patch 400 removably mounted to a reader device 470. The skin-mountable patch 400 has a plurality of microneedles 410 arranged in a ring near the periphery of the skin-mountable patch 400 and protruding from one side (i.e., the bottom side) of the skin-mountable patch 400. The reader device 470 includes a display 473 and buttons 475.

The microneedles 410 have respective first ends configured to penetrate skin and second ends, opposite the first ends, proximate to which the microneedles 410 are attached to the skin-mountable patch 400. The microneedles 410 include respective channels extending from first openings proximate the first ends to second openings proximate the second ends such that interstitial (or other) fluid is received into the channels via the first openings when the microneedles 410 penetrate the skin. Such received interstitial fluid can be directed, via the channels, to a variety of elements of the device 410 (e.g., nanosensors, other types of sensors, sample reservoirs) according to a variety of applications. Further, the microneedles 410 could be used for other applications, for example, to deliver a drug or other substance (e.g., by directing a drug or other substance through channels of the microneedles 410, by having a coating of such a drug, by eluting or otherwise emitting such a drug from material of the microneedles 410).

The reader device 470 could be configured to facilitate mounting of the skin-mountable device 400 on skin of a wearer. For example, the reader device 470 could have an ergonomic shape to ease mounting of the skin-mountable device 400. In some examples, the reader device 470 could include one or more actuators (e.g., a pneumatic cylinder, a solenoid) configured to mount the skin-mountable device 400 to skin such that the microneedles 410 penetrate the skin. Additionally or alternatively, the reader device could provide feedback to a user (e.g., using the display 473, using a vibrator or other haptic feedback element of the reader device 470 (not shown)) to facilitate the user mounting the skin-mountable device 400 to the user's skin using the reader device 470. For example, the reader device 470 could include a force sensor, a displacement sensor, or some other sensor configured to detect a property of the penetration of the microneedles 410 into skin and/or some other property related to mounting the skin-mountable device 400 to skin of the wearer. The reader device 470 could indicate information related to these sensors to inform the wearer's mounting of the skin-mountable device 400 (e.g., the reader device 470 could indicate that an applied mounting force is sufficient to cause the microneedles 410 to penetrate skin to a specified depth). Additionally or alternatively, the reader device 470 could operate the skin-mountable device 400 when the wearer is mounting the skin-mountable device 400 and could indicate information relating to the mounting of the skin-mountable device 400 based on such information. For example, the reader device 470 could operate the skin-mountable device 400 to detect an analyte that is present in interstitial fluid, and could provide an indication when the analyte is detected (implying, e.g., that the microneedles 410 have penetrated skin to a sufficient depth to access interstitial fluid within and/or beneath the skin).

The reader device 470 being configured to removably mount to the skin-mountable device 400 could include the reader device 470 having a shape that conforms to a complementary shape of the skin-mountable device 400. Such a shape could include one or more orienting features to maintain a relative orientation and/or location of the skin-mountable device 400 relative to the reader device. Additionally or alternatively, the reader device 470 and/or skin-mountable device 400 could include magnetic elements, clips, clasps, adhesives, electrostatic elements, hook-and-eye fasteners, snaps, or other elements configured to removably attach, couple, or otherwise mount the skin-mountable device 400 to the reader device 470. Further, one or more electronic, optical, vacuum, microfluidic, or other types of connectors could be included in the skin-mountable device 400 and/or reader device 470 and configured to facilitate the skin-mountable device 400 being removably mounted to the reader device 470.

Figure 4C:
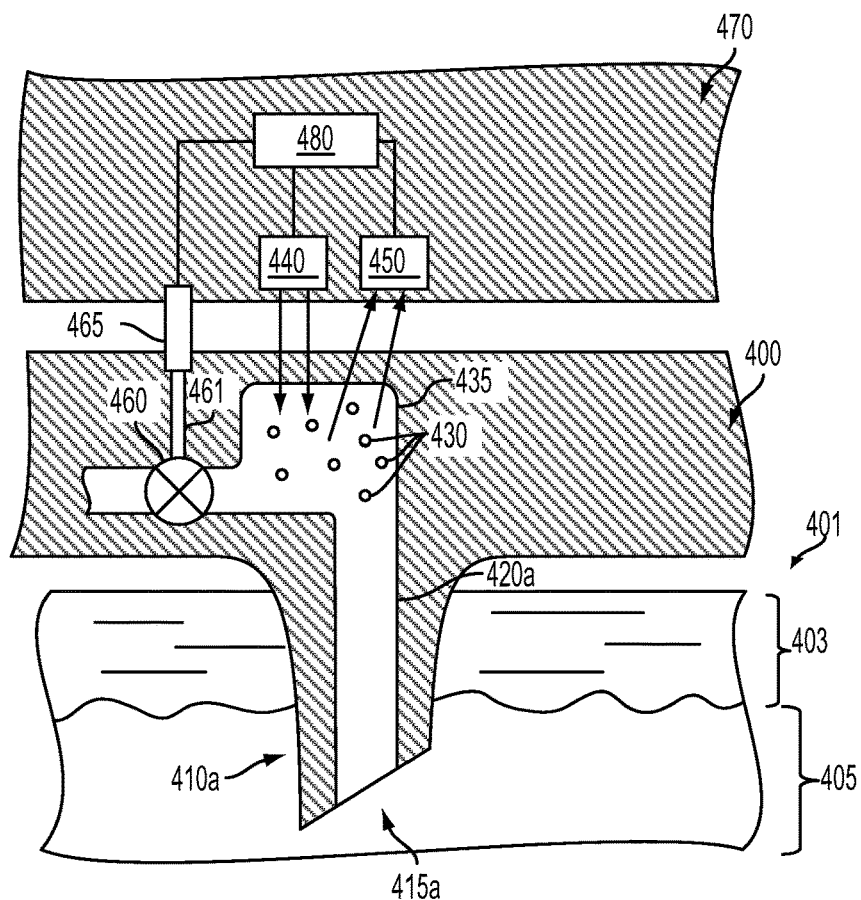
FIG. 4C is a cross-sectional schematic view of a particular microneedle of the example skin-mountable patch and elements of the reader device of FIGS. 4A and 4B when the particular microneedle penetrates skin.

FIG. 4C is a partial cross-sectional view through a portion of skin 401 illustrating elements of the skin-mountable device 400 and the reader device 470. The skin-mountable device 400 includes a particular microneedle 410a that includes a channel 420a extending from a first opening 415a at a first end of the microneedle 410a that is configured to penetrate the skin 401. The channel 420a is connected to a sensing portion 435 that contains a plurality of nanosensors 430 and is configured to direct interstitial fluid received into the channel 420a via the first opening 415a to the nanosensors 430 in the sensing portion 435. A pump 460 is also connected to the sensing portion 435. The reader device 470 includes a light source 440 configured to illuminate the nanosensors 430, a light sensor 450 configured to receive light emitted from the nanosensors 430 (e.g., in response to being illuminated by the light source 440), and a controller 480 configured to operate the light source 440 and light sensor 450. An interconnect 461 connects the pump 460 to a connector 465 configured to provide an electrical connection between the skin-mountable device 400 and the reader device 470 such that the controller 480 can additionally operate the pump 460 when the skin-mountable device 400 is removably mounted to the reader device 470. The skin 401 includes a superficial epidermis 403 and an underlying dermis 405.

The light source 440 and light sensor 450 are configured to illuminate and to receive light emitted from the nanosensors 430. This could include the skin-mountable device 400 and/or the reader device 470 including one or more windows or other elements transparent to wavelengths of light emitted and received, respectively, by the light source 440 and light sensor 450. Additionally or alternatively, the skin-mountable device 400 and/or reader device 470 could have housings or other elements wholly partially composed of such transparent materials. In some examples, the skin-mountable device 400 and/or the reader device 470 could include one or more lenses, mirrors, diffraction gratings, filters, or other optical elements to facilitate the illumination of and/or reception of light emitted from the nanosensors 430 by the light source 440 and light sensor 450, respectively.

The skin-mountable device 400 could include a plurality of sensing portions. Such sensing portion could contain respective different or similar pluralities of nanosensors sensitive to respective different or similar analytes. Further, individual sensing portion could be connected to individual microneedles and/or to sets of microneedles. In such a skin-mountable device 400 (i.e., having a plurality of sensing portions), the reader device could include a plurality of light sources and/or light sensors disposed at respective locations in the reader device 470 corresponding to the locations of the plurality of sensing portions of the skin-mountable device 400. Additionally or alternatively, the reader device 470 could include one or more imagers (e.g., CCD cameras, CMOS cameras, or other multipixel imaging elements) configured to receive light emitted from nanosensors in some or all of the sensing portions.

While the pump 460, as illustrated in FIG. 4, is configured to be operated electronically by the controller 480, thorough the connector 465, the pump 460 or other elements of the skin-mountable device 400 could be actuated and/or operated in some other way(s). For example, the pump 460 could include a magnetic rotor, and the reader device 470 could include a corresponding magnetic rotor configured to exert a force on the rotor of the pump 460 to operate the pump 460. Operation of elements of the skin-mountable device 400 by the reader device 470 could include the reader device 470 exerting a magnetic field, an electric field, an acoustic field, an optical and/or electromagnetic field, or some other energy toward the skin-mountable device 400. In some examples, a pump, vacuum pump, valve, or other fluidic or microfluidic elements could be disposed within the reader device 470 and could be interfaced with elements of the skin-mountable device 400 using a seal, a connector, or some other element(s) configured to couple a vacuum and/or microfluidic system to one or more elements (e.g., the channel 420a, the sensing portion 435) of the skin-mountable device 400.

Further, note that the partitioning of elements between the skin-mountable device 400 and the reader device 470 (i.e., the disposition of the pump 460 in the skin-mountable device 400, the disposition of the controller 480, light sensor 440, and light source 450 in the reader device 470) is intended as a non-limiting example. In other embodiments, more, fewer, or different elements of systems as described herein could be partitioned similarly or differently between one or more skin-mountable or otherwise wearable devices having skin-penetrating microneedles and one or more reader devices or other external devices. In some examples, a pump or other source of vacuum or other microfluidic motive power could be disposed in a reader device and connected to elements of a skin-mountable device (e.g., to channels of microneedles, to sensing portions) via a seal or other vacuum and/or fluid connector or coupler. In some examples, controllers, light sources, light sensors, or other electronic elements could be included in a skin-mountable device and coupled to elements of a reader device via a connector, electrical contacts, or some other means. Additionally or alternatively, a skin-mountable device and a reader device could be configured to communicate wirelessly.

A skin-mountable patch or other device including one or more microneedles as described herein could include a plurality of microneedles configured in a variety of ways. In some embodiments, the plurality of microneedles could be configured to allow for the detection of an analyte using all of the microneedles. Alternatively, the plurality of microneedles could be configured in other ways to allow for other functions, e.g., to allow for the detection of more than one analyte, to allow for the detection of an analyte at a plurality of locations, or other functions or applications.

Figure 5:
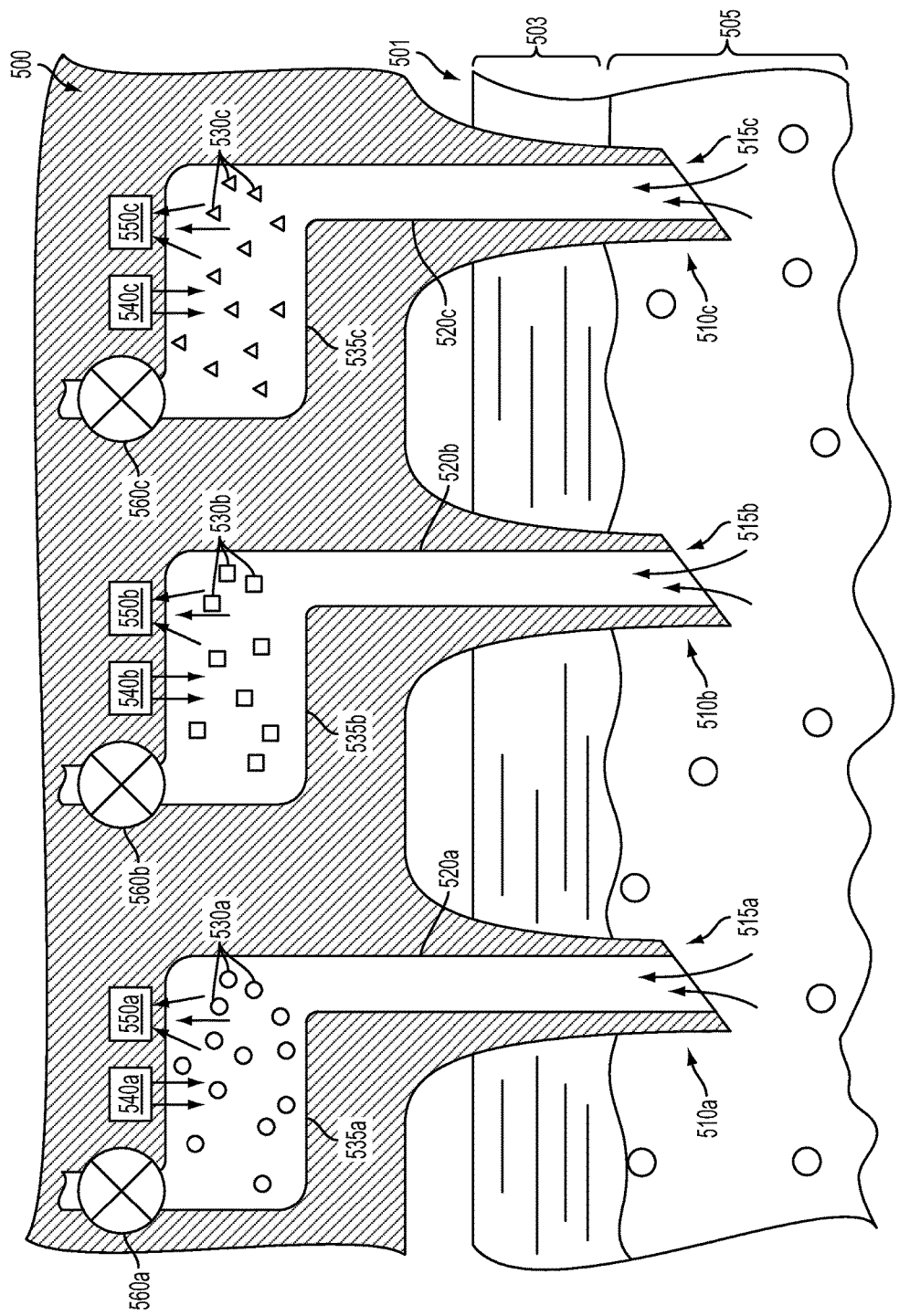
FIG. 5 is a cross-sectional schematic view of microneedles of an example device when the microneedles penetrate skin.

FIG. 5 is a partial cross-sectional view through a portion of skin 501 illustrating a first 510a, second 510b, and third 510c microneedles of a device 500 that penetrate skin 501. The microneedles 510a-c include respective channels 520a, 520b, 520c extending from respective first openings 515a, 515b, 515c at respective first ends of the microneedles 510a, 510b, 510c that are configured to penetrate the skin 501. The channels 520a-c are connected to respective sensing portions 535a, 535b, 535c that contain respective pluralities of nanosensors 530a, 530b, 530c and that are configured to direct interstitial fluid received into the channels 510a-c via respective first openings 515a-c to respective pluralities of nanosensors 530a-c in respective sensing portions 535a-c. Pumps 560a, 560b, 560c are also connected to respective sensing portions 535a-c. Light sources 540a, 540b, 540c are configured to illuminate respective pluralities of nanosensors 530a-c and light sensors 550a, 550b, 550c are configured to receive light emitted from respective pluralities of nanosensors 530a-c (e.g., in response to being illuminated by the light sources 540a-c). The skin 501 includes a superficial epidermis 503 and an underlying dermis 505.

As illustrated in FIG. 5, the pluralities of nanosensors 530a-c comprise different types of nanosensors. The pluralities of nanosensors 530a-c could be configured to selectively interact with different respective analytes. Alternatively, the pluralities of nanosensors 530a-c could be configured to selectively interact with the same analyte. Configured in this way, the device 500 could be operated (e.g., the pumps 560a-c could be operated to draw interstitial fluid through the sensing portions 353a-c and the light sources 540a-c and light sensors 550a-c could be operated to detect optical properties of the nanosensors 530a-c) to detect the analyte at a plurality of points in skin corresponding to the locations of the first openings 515a-c (e.g., such a device could be operated to map, e.g., the concentration of the analyte across an area of skin).

Elements (e.g., pumps, sensing portions, light sensors, light sources, detectors, pluralities of nanosensors, valves, etc.) could be shared between microneedles. For example, a single pump, sensing portion, and plurality of nanosensors could be configured to receive interstitial fluid through a plurality of microneedles. This could allow a single pump, sensing portion, or other elements to be used to detect an analyte within a larger region than when attached to a single microneedle. Additionally or alternatively, a plurality of valves could be disposed between the microneedles and the single pump, sensing portion, or other in-common element, and the valves could be operated to allow the in-common element(s) to be used alternatively to operate with individual microneedles and/or sets of microneedles. For example, a plurality of microneedles could be connected, via individual valves, to an in-common sensing portion (containing nanosensors) that is further connected to an in-common pump. The pump and valves could be operated such that, during sequential, non-overlapping periods of time, interstitial fluid in the sensing portion is drawn for individual microneedles of the plurality of microneedles.

Note that descriptions herein relating to the control of fluids received through one or more microneedles, and the application of such to one or more individual or in-common elements, could be applied with some modification to the transdermal delivery of drugs, ions, or other substances through the one or more microneedles. For example, a single drug reservoir and/or pump could be connected, via a plurality of respective valves, to a plurality of channels of microneedles. Further, valves, pumps, and other microfluidic elements could be configured to allow for the use of a single needle alternatively to transdermally deliver substances and to receive interstitial fluid for sampling. For example, a particular microneedle could be operated, during a first period of time, to receive interstitial fluid from skin and to deliver the interstitial fluid to a detector (e.g., a sensing portion, nanosensors, light source, and light sensor) to detect an analyte in the fluid. Responsive to detection of the analyte, the microneedle could be operated, during a second period of time, to transdermally deliver a drug, ion, metabolite, or other substance through and/or into the skin. Other configurations and applications of devices as described herein are anticipated.

IV. Example Electronics

Figure 6:
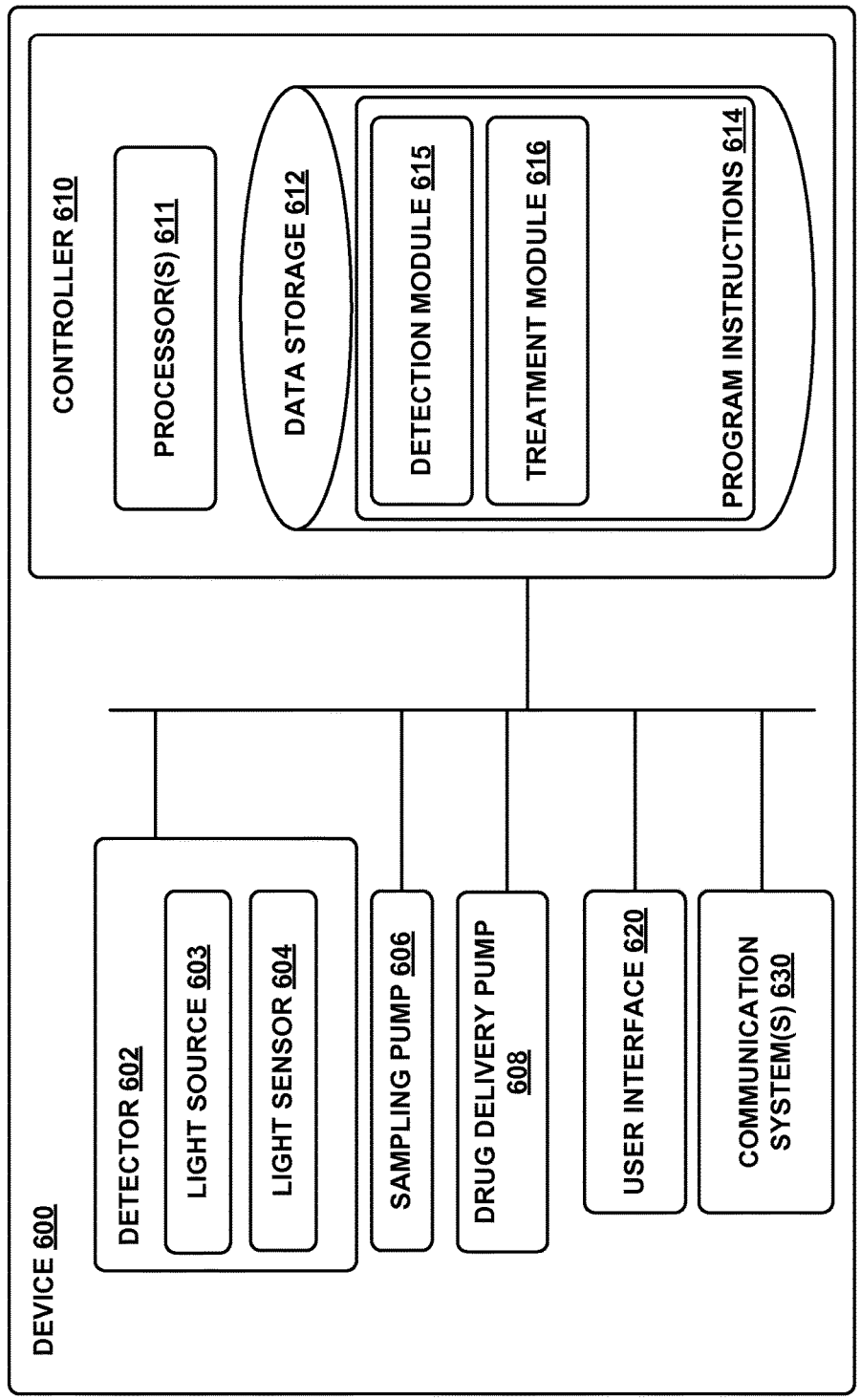
FIG. 6 is a functional block diagram of an example device.

FIG. 6 is a simplified block diagram illustrating the electronic components of a device 600, according to an example embodiment. Device 600 may take the form of or be similar to one of the example devices 100, 200, 300a, 300b, 300c, 400, 470, or 500 shown in FIGS. 1A-C, 2, 3A-C, 4A-C, or 5. Device 600 may take a variety of forms, such as a skin-mountable device or some other otherwise wearable device including one or more microneedles as described herein. Device 600 could also take the form of a reader device or other system configured to interface with such a skin-mounted or otherwise wearable device (e.g., by being removably mounted to the skin-mounted or otherwise wearable device) to facilitate functions of the skin-mountable or otherwise wearable device. A skin-mountable or otherwise wearable device, a reader device, or some other device could include more or fewer elements than those illustrated. Further, the illustrated elements could be divided between multiple devices to provide the functions described herein. For example, a sampling pump (e.g., 606) could be provided in a skin-mountable patch, while a detector (e.g., 602) is provided in a reader device configured to be removably mounted to the skin-mountable patch. Device 600 also could take other forms.

In particular, FIG. 6 shows an example of a device 600 having a light source a detector 602 that includes a light source 603 and light sensor 604, a sampling pump 606, a drug delivery pump 608, a user interface 620, communication system(s) 630 for transmitting data to a remote system, and controller 610. The components of the device 600 may be disposed on or within a housing of a skin-mountable patch or reader device or on some other structure for mounting the device such that mount microneedles of the device 600 penetrate skin or such that the device 600 can be removably mounted to such a skin-mountable patch such that the detector 602 could optically detect optical properties of nanosensors exposed to interstitial fluid from beneath and/or within skin of a person. The device 600 could include additional components, for example, additional or alternative sensors or some other component(s) according to an application.

Controller 610 may be provided as a computing device that includes one or more processors 611. The one or more processors 611 can be configured to execute computer-readable program instructions 614 that are stored in a computer readable data storage 612 and that are executable to provide the functionality of device 600 as described herein.

The computer readable data storage 612 may include or take the form of one or more non-transitory, computer-readable storage media that can be read or accessed by at least one processor 611. The one or more computer-readable storage media can include volatile and/or non-volatile storage components, such as optical, magnetic, organic or other memory or disc storage, which can be integrated in whole or in part with at least one of the one or more processors 611. In some embodiments, the computer readable data storage 612 can be implemented using a single physical device (e.g., one optical, magnetic, organic or other memory or disc storage unit), while in other embodiments, the computer readable data storage 612 can be implemented using two or more physical devices.

The detector 602 is configured to optically detect an optical property of nanosensors that changes in response to interaction of the nanosensors with an analyte. As illustrated, the detector includes the light source 603 and the light sensor 604. However, the detector 602 could include additional or alternative elements configured to detect the optical property and/or to detect some other property of the analyte via some other method. For example, the detector 602 could include one or more electrochemical or other sensors configured to detect the presence of the analyte in a fluid when directly exposed to the fluid. In some examples, the detector could include multiple light sources and/or multiple light sensors to enable detection of optical properties of multiple pluralities of nanosensors disposed in a plurality of respective locations and/or configured to have optical properties that change based on the presence of a plurality of respective different analytes.

The light source 603 is configured to illuminate nanosensors with illumination at one or more specified wavelengths. The nanosensors could be disposed in a sensing portion, a chamber, a channel of a microneedle, or in some other region or environment such that the nanosensors are exposed to interstitial fluid and further such that an optical property of the nanosensors can be affected by the presence of an analyte in the interstitial fluid. Further, the light source 603 could emit illumination at a fixed wavelength, a controllable wavelength (e.g., illumination that is substantially monochromatic, but having a wavelength that can be altered by operation of the light source) and/or at a range of wavelengths (e.g., a broadband or white illumination source across some specified range of wavelengths).

The light sensor 604 includes at least one light-sensitive element configured to detect light within a particular specified narrow range of wavelengths (e.g., by including a filter, a prism and other optics, and/or having an intrinsic sensitivity to the light across the range of wavelengths) and/or configured to be sensitive to broad range of wavelengths of light (e.g., broadband light-sensitive elements). The light sensor 604 could include one or more photodiodes, phototransistors, photoresistors, active pixel sensors, CMOS pixel arrays, CCD elements, filters, lens, or other elements.

The sampling pump 606 is configured to apply a suction or otherwise pump fluid such that interstitial fluid is drawn through a channel of a microneedle and directed to a plurality of nanosensors. The drug delivery pump 608 is configured to pump a drug, ion, metabolite, or other substance such that the pumped substance is transdermally delivered through and/or into skin of a wearer. This could include pumping such substances through a channel of a microneedle. The pumps 606, 608 could be peristaltic pumps, centrifugal pumps, impedance pumps, microfluidic pumps, or some other type(s) of pumps. The pump(s) 606, 608 could be operated by exerting an electrical voltage, an electrical current, a magnetic field, an electric field, an acoustic field, an optical and/or electromagnetic field, or some other energy on and/or through one or more elements of the pump(s) 606, 608. For example, the reader device could emit a beam of light toward elements of a microfluidic pump to effect a fluid flow (e.g., a flow of interstitial fluid, a drug, or some other substance through a microneedle).

The program instructions 614 stored on the computer readable data storage 612 may include instructions to perform any of the methods described herein. For instance, in the illustrated embodiment, program instructions 614 include a detection module 615 and a treatment module 616.

The detection module 615 can include instructions for operating the detector 602, light source 603, light sensor 604, and/or sampling pump 606 to enable any of the functions or applications of a device to detect an analyte in interstitial fluid from within and/or beneath skin as described herein. Generally, instructions in the detection module 615 describe methods of operating the light source 603 to illuminate nanosensors with light at one or more specified wavelengths during one or more respective periods of time. Instructions in the detection module 615 further describe methods of operating the light sensor 604 to receive light from illuminated nanosensors and to detect (e.g., to detect the presence, concentration, or other information about) an analyte that is interacting with the nanosensors. The detection module 615 could additionally include instructions to operate the sampling pump 606, valves, or other microfluidic elements to receive interstitial fluid through a channel of a microneedle and to direct the received interstitial fluid to the nanosensors. Other operations, functions, and applications of the detector 602, light source 603, light sensors 604, sampling pump 606, and/or of other components of the device 600 as described herein could be implemented as program instructions in the detection module 615.

The treatment module 616 can include instructions for planning and/or executing the transdermal delivery of a drug, ion, metabolite, or other substance. The instructions could include instructions to determine a dose amount, a dose rate, a dose timing, or other information describing a transdermal drug delivery based on a presence and/or amount of a detected analyte at one or more points in time and/or on information about transdermal drug delivery in the past. Such determinations could additionally or alternatively be based on information and/or commands from a remote system (e.g., from a server in a physician's office that a physician could use to update parameters of a drug therapy implemented wholly or partially using the device 600). Instructions of the treatment module 616 can further include instructions for controlling the drug delivery pump 608, valves, or other components of the device 600 to effect transdermal delivery of a drug or other substance according to a drug delivery determination as described above.

The treatment module 616 could additional include instruction for determining whether a medical condition is indicated based on at least the corresponding presence, concentration, or other property of the detected analyte. These instructions could be executed at each of a set of preset measurement times. In response to a determination by the treatment module 616 that a medical or other specified condition is indicated, the treatment module 616 may generate an alert via the user interface 620. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication. Additionally or alternatively, the treatment module 616 may transmit an alert, via the communication system(s) 630, to a physician, the police, emergency medical services, or some other emergency service.

Some of the program instructions of the detection module 615 and/or treatment module 616 may, in some examples, be stored in a computer-readable medium and executed by a processor located external to the device 600. For example, the device 600 could be configured to illuminate and to receive light from nanosensors and then transmit related data to a remote server, which may include a reader device, a mobile device, a personal computer, the cloud, or any other remote system, for further processing (e.g., for the determination of spectrographic content of the received light, for determining a concentration of the analyte based on the received light).

User interface 620 could include indicators, displays, buttons, touchscreens, head-mounted displays, and/or other elements configured to present information about the device 600 to a user and/or to allow the user to operate the device 600. Additionally or alternatively, the device 600 could be configured to communicate with another system (e.g., a reader device, a cellphone, a tablet, a computer, a remote server) and to present elements of a user interface using the remote system. The user interface 620 could be configured to allow a user to specify some operation, function, or property of operation of the device 600. Other configurations and methods of operation of a user interface 620 are anticipated.

Communication system(s) 630 may also be operated by instructions within the program instructions 614, such as instructions for sending and/or receiving information via a wireless antenna, which may be disposed on or in the device 600. The communication system(s) 630 can optionally include one or more oscillators, mixers, frequency injectors, etc. to modulate and/or demodulate information on a carrier frequency to be transmitted and/or received by the antenna. In some examples, the device 600 is configured to indicate an output from the controller 610 by transmitting an electromagnetic or other wireless signal according to one or more wireless communications standards (e.g., Bluetooth, WiFi, IRdA, ZigBee, WiMAX, LTE). In some examples, the communication system(s) 630 could include one or more wired communications interfaces and the device 600 could be configured to indicate an output from the controller 610 by operating the one or more wired communications interfaces according to one or more wired communications standards (e.g., USB, FireWire, Ethernet, RS-232).

The computer readable data storage 612 may further contain other data or information, such as medical and health history of a wearer from whose skin interstitial fluid is being accessed and analyzed or otherwise interacted with by the device 600. Further, the computer readable data storage 612 may contain calibration data corresponding to a configuration of the device 600 or some other information. Calibration, model, and/or other data may also be generated by a remote server and transmitted to the device 600 via communication system(s) 630.

In some examples, the collected calibration and/or model data, stored information about operation of the device 600 (e.g., information about detected analytes detected using the device 600), health state information (e.g., health state of a wearer) detected by the device 600 and other usage or other information may additionally be input to a cloud network (e.g., using the communications system(s) 630) and be made available for download by users having sufficient permissions (e.g., a doctor tasked with reviewing the health of a wearer). Other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring outcomes of a surgical intervention, drug therapy, or other treatment. For example, high-density, real-time data may be collected from a population of device users who have experienced a drug delivery using information generated by the device 600 to assess the safety and efficacy of the drug and/or of the drug therapy. Such data may also be used on an individual level to assess a particular patient's response to a drug therapy. Based on this data, a physician or clinician may be able to tailor future drug delivery or other treatment to suit an individual's needs.

V. Example Methods

Figure 7:
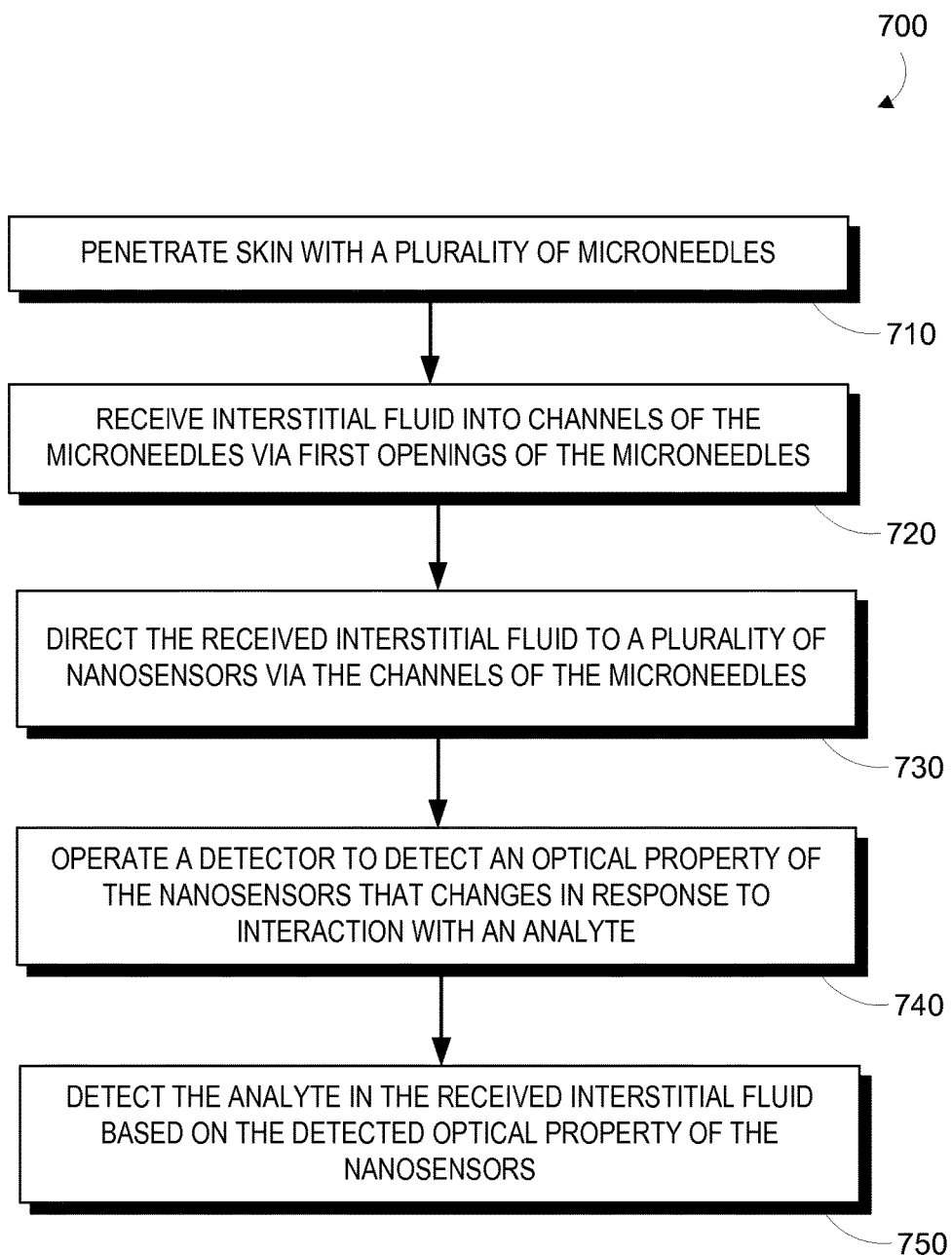
FIG. 7 is a flowchart of an example method.

FIG. 7 is a flowchart of an example method 700 for detecting an analyte in interstitial fluid using a plurality of microneedles to access the interstitial fluid from outside of a body containing the interstitial fluid. Each microneedle of the plurality of microneedles includes a first end that is configured to penetrate skin, a second end opposite the first end, and a channel that extends from a first opening proximate the first end to a second opening proximate the second end. The method 700 also includes steps involving a plurality of nanosensors. Each nanosensor includes a nanoparticle and is configured to selectively interact with an analyte that is present in the interstitial fluid. Each nanosensor is further configured to have an optical property that changes in response to interaction with the analyte.

The method 700 includes penetrating skin with the plurality of microneedles (710). This could include manually pressing the microneedles against the skin with a force sufficient to cause the microneedles to penetrate the skin. This (710) could include operating a reader device that is configured to facilitate mounting of the microneedles and/or a system of which the microneedles are a part to the skin. For example, the reader device could have an ergonomic shape to ease mounting of the system. In some examples, the method 700 could further include removably mounting a skin-mountable patch that includes the plurality of microneedles and the nanosensors to a reader device. In some examples, penetrating skin with the plurality of microneedles (710) could include operating one or more actuators (e.g., pneumatic cylinders, solenoids) configured to mount the microneedles and/or a system of which the microneedles are a part to skin such that the microneedles penetrate the skin. In some examples, penetrating skin with the plurality of microneedles (710) could include performing one or more operations (e.g., applying a force to the microneedles) based on the output of a force sensor, a displacement sensor, or some other sensor configured to detect a property of the penetration of the microneedles into skin and/or some other property related to mounting the microneedles and/or a system of which the microneedles are a part to skin.

The method 700 additionally includes receiving interstitial fluid into the channels of the microneedles via the first openings of the microneedles (720). The method 700 further includes directing the received interstitial fluid to a plurality of nanosensors via the channels of the microneedles (730). In some examples, this could include the nanosensors being disposed within the channels of the microneedles. In some examples, this could include operating a valve, pump, or other microfluidic element(s) connected between the channels of the microneedles and a sensing portion or other region containing the nanosensors. In some examples, the method 700 could further include operating a pump control a flow rate of the received interstitial fluid though the channels of the microneedles.

The method 700 additionally includes operating a detector to detect the optical property of the nanosensors (740). This could include operating a light source of the detector to illuminate the nanosensors with light at an excitation wavelength of a fluorophore of the nanosensors. This could further include operating a light sensor of the detector to receive light responsively emitted by the nanosensors at an emission wavelength of the fluorophore of the nanosensors. Additionally or alternatively, operating the detector to detect the optical property of the nanosensors (740) could include operating a light source of the detector to output a plurality of lights having a respective plurality of properties (e.g., wavelengths, polarizations, spectral contents) to illuminate the nanosensors and/or operating a light sensor of the detector to detect one or more properties (e.g., amplitude, polarization, coherence, spectral content) of responsively emitted light from the nanosensors.

The method 700 additionally includes detecting an analyte in the interstitial fluid based on the detected optical property of the nanosensors (750). This could include receiving from the detector one or more detected amplitudes or other properties of light received from the nanosensors within one or more respective ranges of wavelengths. This (750) could include determining that an amplitude of the received light within a specified range of wavelengths (e.g., a range of wavelengths corresponding to an emission wavelength of a fluorophore of the nanosensors) is above a specified and/or determined threshold, and based on this determination determining that the analyte is present. This (750) could include determining that an amplitude of the received light within a first specified range of wavelengths (e.g., a range of wavelengths corresponding to an emission wavelength of a fluorophore of the nanosensors) relative to an amplitude of the received light within a second specified range of wavelengths (e.g., a range of wavelengths within which the nanosensors emit substantially no light in response to illumination by the detector) indicated the presence of the analyte. The method 700 could further include determining a concentration or other information about the analyte in the interstitial fluid based on the detected optical property of the nanosensors.

The method 700 could include additional steps. For example, the method could include operating the detector, or a further detector of the system, to detect an optical property of a further plurality of nanosensors and to detect a further analyte in the interstitial fluid based on the detected optical property of the further nanosensors. In some examples, the method 720 could include operating the detector to detect the optical property of the nanosensors (740) and detecting an analyte in the interstitial fluid based on the detected optical property (750) a plurality of times during a plurality of respective periods of time, e.g., to monitor the analyte over a protracted time period. The method 700 could include controlling transdermal delivery (e.g., using a pump and one or more of the microneedles, and/or one or more additional microneedles of the system) of a drug, ion, metabolite, or other substance based on the detected analyte (e.g., based on a detected concentration of the analyte, to control and/or effect a health state of a wearer of the system).

The method 700 could include other additional steps or elements. The method 700 could include any additional steps, or could include details of implementation of the listed steps 710, 720, 730, 740, 750 or of other additional steps, as described herein in relation to the operation of a skin-mountable patch, wearable device, reader device, or other systems or devices as described herein. Additional and alternative steps of the method 700 are anticipated. The example method 700 illustrated in FIG. 7 is meant as an illustrative, non-limiting example. Additional or alternative elements of the method and additional or alternative components of the wearable device are anticipated, as will be obvious to one skilled in the art.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a plurality of nanosensors, wherein each nanosensor comprises a nanoparticle and an analyte-selective agent that selectively interacts with an analyte present in interstitial fluid, wherein the analyte-selective agent is disposed on a surface of the nanoparticle or within an interior of the nanoparticle, and wherein each nanosensor has an optical property that changes in response to interaction with the analyte;

a detector;

a plurality of microneedles, wherein each microneedle comprises (i) a first end shaped to penetrate skin, (ii) a second end opposite the first end, and (iii) a channel that extends from a first opening proximate the first end to a second opening proximate the second end such that interstitial fluid is received into the channel via the first opening when the microneedle penetrates the skin, and wherein the nanosensors are disposed relative to the microneedles such that the microneedles direct the received interstitial fluid to the nanosensors via the channels; and a controller operably coupled to the detector, wherein the controller comprises a processor and data storage that stores program instructions, wherein the program instructions are executable by the processor to perform controller operations comprising:

operating the detector to detect the optical property of the nanosensors; and detecting the analyte in the received interstitial fluid based on the detected optical property of the nanosensors, wherein the analyte is an ion; and wherein each nanosensor comprises:

an ionophore, wherein the ionophore selectively interacts with the ion;

a linking agent, wherein the linking agent changes a local pH in response to the ionophore selectively interacting with the ion; and a fluorophore, wherein the fluorophore is a pH-sensitive fluorophore having a fluorescent property that is dependent upon the local pH.

2. The system of claim 1, further comprising:

a plurality of further nanosensors, wherein each further nanosensor comprises a nanoparticle that selectively interacts with a further analyte present in interstitial fluid, and wherein each further nanosensor has an optical property that changes in response to interaction with the further analyte;

a further detector, wherein the controller is operably coupled to the further detector;

a plurality of further microneedles, wherein each further microneedle comprises (i) a first end shaped to penetrate skin, (ii) a second end opposite the first end, and (iii) a further channel that extends from a first opening proximate the first end to a second opening proximate the second end such that interstitial fluid is received into the channel via the first opening when the further microneedle penetrates the skin, wherein the further nanosensors are disposed relative to the further microneedles such that the further microneedles direct the interstitial fluid to the further nanosensors via the channels, and wherein the controller operations further comprise:

operating the further detector to detect the optical property of the further nanosensors; and detecting the further analyte in the received interstitial fluid based on the detected optical property of the further nanosensors.

3. The system of claim 1, wherein operating the detector to detect the optical property of the nanosensors comprises:

illuminating the nanosensors, using a light source of the detector, with light at an excitation wavelength of the fluorophore; and receiving light emitted from the nanosensors in response to the illumination at an emission wavelength of the fluorophore, using a light sensor of the detector.

4. The system of claim 1, wherein the detector and the controller are disposed in a reader device, wherein the microneedles and nanosensors are disposed in a skin-mountable patch, and wherein the reader device is reversibly mountable to the skin-mountable patch.

5. The system of claim 4, wherein the reader device comprises one or more actuators to mount the skin-mountable patch to skin such that the microneedles penetrate the skin.

6. The system of claim 1, wherein the system comprises a wearable device mountable to skin such that the microneedles penetrate the skin, wherein the wearable device comprises the detector, the microneedles, the nanosensors, and the controller.

7. The system of claim 1, wherein each microneedle further comprises a hydrophilic coating disposed on an inside surface of the channel.

8. The system of claim 1, wherein the nanosensors are disposed within the channels of the microneedles.

9. The system of claim 1, wherein the nanosensors are disposed outside of the channels of the microneedles and proximate to the second ends of the microneedles, such that the microneedles direct the received interstitial fluid to the nanosensors via the channels and the second openings.

10. The system of claim 1, further comprising a pump coupled to the microneedles, wherein the pump controls a flow rate of the received interstitial fluid through the channels of the microneedles.

11. The system of claim 1, further comprising:

a drug reservoir that stores an amount of a drug, wherein the controller operations further comprise:

controlling transdermal delivery of the drug based on the detected analyte.

12. A method comprising:

penetrating skin with a plurality of microneedles, wherein each microneedle comprises (i) a first end configured to penetrate the skin, (ii) a second end opposite the first end, and (iii) a channel that extends from a first opening proximate the first end to a second opening proximate the second end;

receiving interstitial fluid into the channels of the microneedles via the first openings of the microneedles;

directing the received interstitial fluid to a plurality of nanosensors via the channels of the microneedles, wherein each nanosensor comprises a nanoparticle and an analyte-selective agent that selectively interacts with an analyte present in the interstitial fluid, wherein the analyte-selective agent is disposed on a surface of the nanoparticle or within an interior of the nanoparticle, and wherein each nanosensor has an optical property that changes in response to interaction with the analyte;

operating a detector to detect the optical property of the nanosensors; and detecting the analyte in the received interstitial fluid based on the detected optical property of the nanosensors, wherein the analyte is an ion; and wherein each nanosensor comprises:

an ionophore, wherein the ionophore selectively interacts with the ion;

a linking agent, wherein the linking agent changes a local pH in response to the ionophore selectively interacting with the ion; and a fluorophore, wherein the fluorophore is a pH-sensitive fluorophore having a fluorescent property that is dependent upon the local pH.

13. The method of claim 12, wherein operating the detector to detect the optical property of the nanosensors comprises:

illuminating the nanosensors, using a light source of the detector, with light at an excitation wavelength of the fluorophore; and receiving light emitted from the nanosensors in response to the illumination at an emission wavelength of the fluorophore, using a light sensor of the detector.

14. The method of claim 12, further comprising:

controlling a flow rate of the received interstitial fluid through the channels of the microneedles using a pump.

15. The method of claim 12, wherein operating the detector to detect the optical property of the nanosensors and detecting the analyte in the received interstitial fluid based on the detected optical property of the nanosensors are performed a plurality of times during a plurality of respective periods of time.

16. The method of claim 12, wherein directing the received interstitial fluid to a plurality of nanosensors via the channels of the microneedles comprises:

directing the received interstitial fluid to the plurality of nanosensors via the channels and second openings of the microneedles.

17. The method of claim 12, further comprising:

controlling transdermal delivery of a drug based on the detected analyte.

18. The method of claim 12, wherein detecting the analyte in the received interstitial fluid based on the detected optical property of the nanosensors comprises determining a concentration of the analyte in the received interstitial fluid.

19. The method of claim 12, wherein the microneedles and nanosensors are disposed in a skin-mountable patch, wherein the detector is disposed in a reader device removably mountable to the skin-mountable patch, and wherein operating the detector to detect the optical property of the nanosensors comprises:

operating the detector to detect the optical property of the nanosensors while the reader device is mounted to the skin-mountable patch.

* * * * *